US010980920B2

(12) United States Patent
Sharma et al.

(10) Patent No.: US 10,980,920 B2
(45) Date of Patent: Apr. 20, 2021

(54) IN SITU FORMING HEMOSTATIC FOAM IMPLANTS

(71) Applicant: ARSENAL MEDICAL, INC., Watertown, MA (US)

(72) Inventors: Upma Sharma, Somerville, MA (US); Irina Gitlin, Brookline, MA (US); Gregory T. Zugates, Chelmsford, MA (US); Adam Rago, Falmouth, MA (US); Parisa Zamiri, Brookline, MA (US); Rany Busold, Medford, MA (US); Robert J. Caulkins, Watertown, MA (US); Toby Freyman, Lexington, MA (US); Quynh Pham, Methuen, MA (US); Changcheng You, Northbridge, MA (US); Jeffrey Carbeck, Belmont, MA (US)

(73) Assignee: Arsenal Medical, Inc., Watertown, MA (US)

( * ) Notice: Subject to any disclaimer, the term of this patent is extended or adjusted under 35 U.S.C. 154(b) by 262 days.

(21) Appl. No.: 15/923,003

(22) Filed: Mar. 16, 2018

(65) Prior Publication Data

US 2018/0250446 A1 Sep. 6, 2018

Related U.S. Application Data

(60) Continuation of application No. 14/928,857, filed on Oct. 30, 2015, now Pat. No. 10,307,515, which is a (Continued)

(51) Int. Cl.
*A61F 2/02* (2006.01)
*A61L 31/06* (2006.01)
(Continued)

(52) U.S. Cl.
CPC ........ *A61L 31/06* (2013.01); *A61B 17/12031* (2013.01); *A61B 17/12163* (2013.01);
(Continued)

(58) Field of Classification Search
CPC ...................... A61F 2/02; A61F 2/0063; A61F 2002/30062; A61F 2/04; A61F 2/12163;
(Continued)

(56) References Cited

U.S. PATENT DOCUMENTS

| | | | |
|---|---|---|---|
| 6,211,259 | B1 | 4/2001 | Borden et al. |
| 7,815,928 | B2 | 10/2010 | Cherif Cheikh |

(Continued)

FOREIGN PATENT DOCUMENTS

| | | |
|---|---|---|
| WO | 0211975 | 2/2002 |
| WO | 2006055261 | 5/2006 |

OTHER PUBLICATIONS

Burlew et al., Preperitoneal pelvic packing/external fixation with secondary angioembolization: optimal care for life-threatening hemorrhage from unstable pelvic fractures, Dec. 2010, Journal of the American College of Surgeons, Apr. 2011 212(4), pp. 628-635.

*Primary Examiner* — Vi X Nguyen
(74) *Attorney, Agent, or Firm* — Kacvinskv Daisak Bluni PLLC

(57) ABSTRACT

Systems and methods related to polymer foams are generally described. Some embodiments relate to compositions and methods for the preparation of polymer foams, and methods for using the polymer foams. The polymer foams can be applied to a body cavity and placed in contact with, for example, tissue, injured tissue, internal organs, etc. In some embodiments, the polymer foams can be formed within a body cavity (i.e., in situ foam formation). In addition, the foamed polymers may be capable of exerting a pressure on
(Continued)

an internal surface of a body cavity and preventing or limiting movement of a bodily fluid (e.g., blood, etc.).

11 Claims, 21 Drawing Sheets

Related U.S. Application Data division of application No. 13/209,020, filed on Aug. 12, 2011, now Pat. No. 9,173,817, which is a continuation-in-part of application No. 12/862,362, filed on Aug. 24, 2010, now abandoned.

(60) Provisional application No. 61/368,095, filed on Jul. 27, 2010, provisional application No. 61/236,314, filed on Aug. 24, 2009.

(51) Int. Cl.

| | |
|---|---|
| ***A61J 1/20*** | (2006.01) |
| ***A61L 27/18*** | (2006.01) |
| ***A61L 27/56*** | (2006.01) |
| ***A61L 27/58*** | (2006.01) |
| ***A61L 31/14*** | (2006.01) |
| ***A61M 37/00*** | (2006.01) |
| ***A61B 17/12*** | (2006.01) |
| ***C08L 63/00*** | (2006.01) |

(52) U.S. Cl.

CPC ....... *A61B 17/12186* (2013.01); *A61J 1/2093* (2013.01); *A61L 27/18* (2013.01); *A61L 27/56* (2013.01); *A61L 27/58* (2013.01); *A61L 31/141* (2013.01); *A61L 31/146* (2013.01); *A61L 31/148* (2013.01); *A61M 37/00* (2013.01); *C08L 63/00* (2013.01); *A61B 2017/12004* (2013.01); *A61L 2400/04* (2013.01); *A61L 2400/06* (2013.01); *A61L 2400/18* (2013.01)

(58) Field of Classification Search

CPC ........ A61B 17/12031; A61B 17/12163; A61B 17/12; A61L 27/3604; A61L 27/3687

See application file for complete search history.

(56) References Cited

U.S. PATENT DOCUMENTS

| | | | |
|---|---|---|---|
| 2002/0147462 A1 | 10/2002 | Mair et al. | |
| 2003/0014075 A1 | 1/2003 | Rosenbluth et al. | |
| 2003/0118692 A1 | 6/2003 | Wang et al. | |
| 2006/0008419 A1* | 1/2006 | Hissink ............... | A61L 24/0036 424/45 |
| 2007/0005140 A1 | 1/2007 | Kim et al. | |
| 2009/0232877 A1 | 9/2009 | Montes et al. | |
| 2011/0202016 A1 | 8/2011 | Zugates | |
| 2011/0237994 A1 | 9/2011 | Russ | |
| 2012/0107439 A1 | 5/2012 | Sharma | |
| 2013/0110066 A1 | 5/2013 | Sharma | |

* cited by examiner 10
10
12
16
14
FIRST CHAMBER
SECOND CHAMBER

| Transport Score | Interpretation |
|---|---|
| 0 | Carrier does not reach spleen segment |
| 1 | Carrier reaches spleen segment, but does not contact injured surface |
| 2 | Carrier is in incomplete contact with injured surface |
| 3 | Carrier is in complete contact with injured surface or partially envelopes segment |
| 4 | Carrier completely envelopes spleen segment |

*Table 1: Semi-quantitative transport scoring system for in vivo studies.*

FIG. 19A

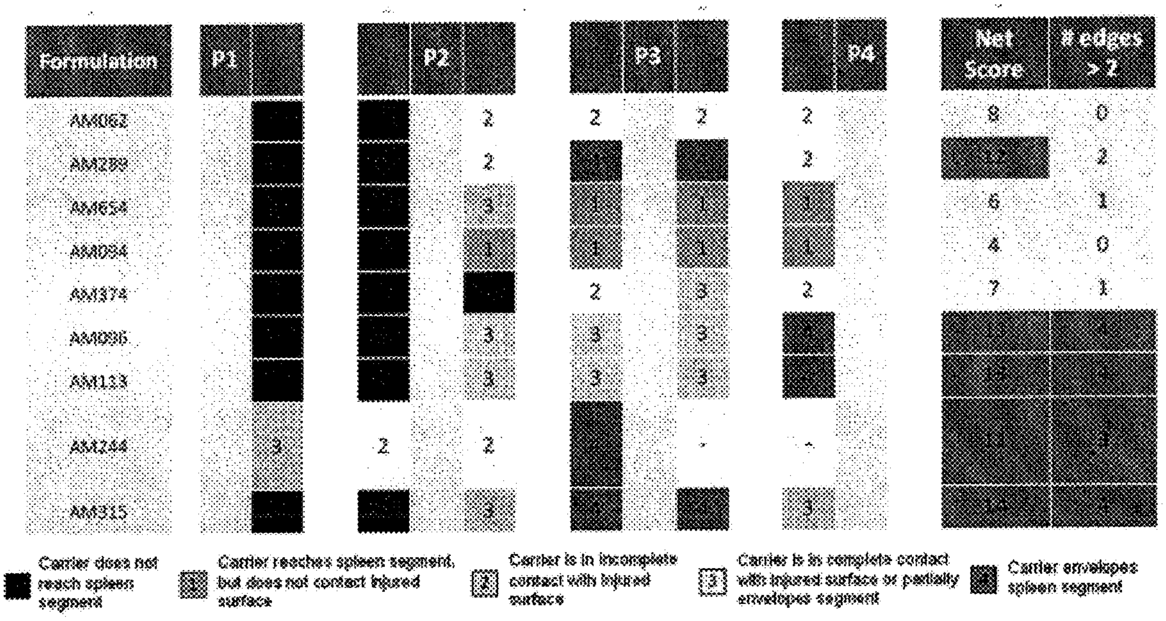

*Table 2: Summary of in vivo transport scores by material. The grade V splenic injury creates four splenic pieces and six cut surfaces. Each was scored using the semi-quantitiative transport scoring system. Cumulative score and the number of edges with a score greater than two is summarized at the right.*

FIG. 19B

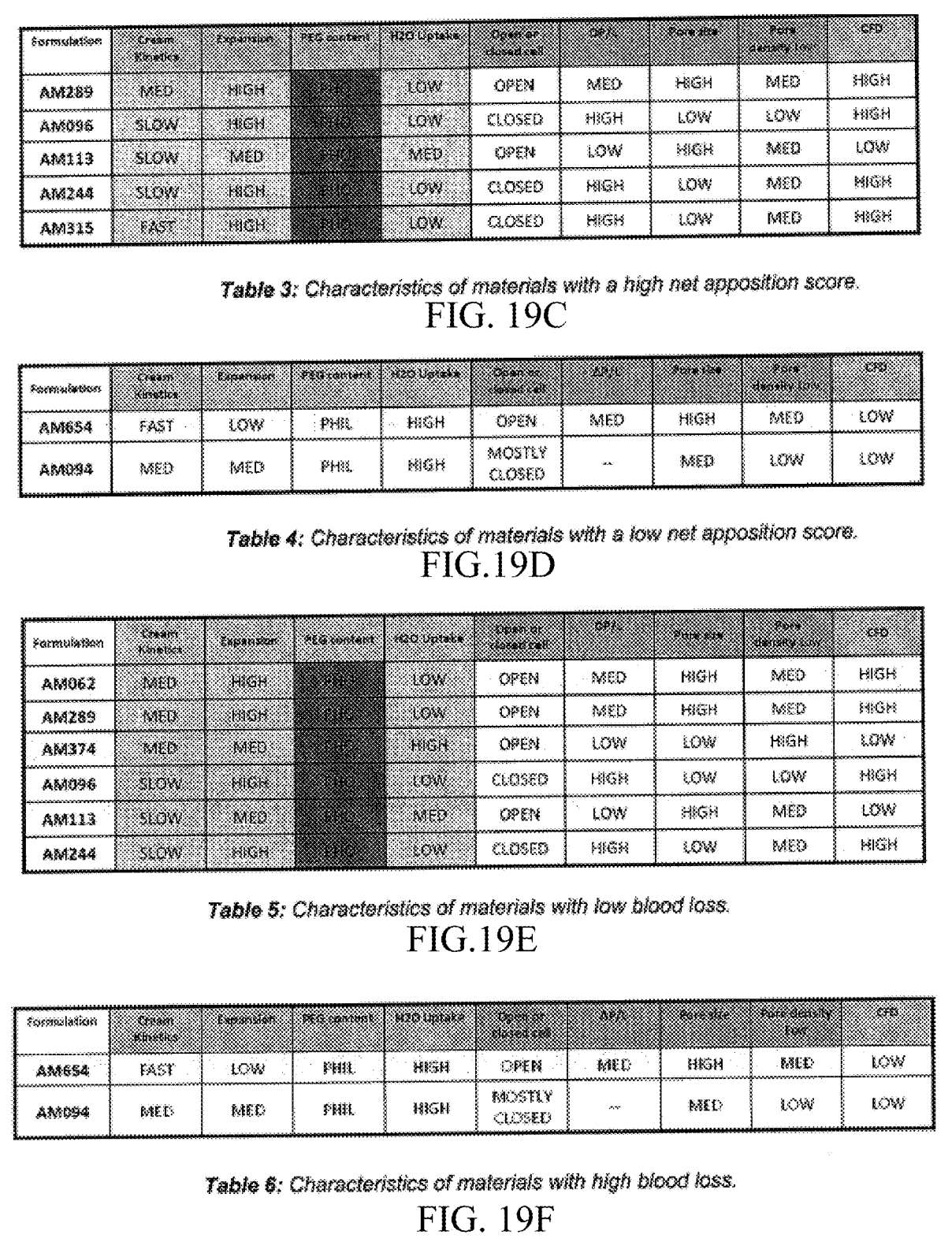

| Formulation | Cream Kinetics | Expansion | PEG content | H2O Uptake | Open or closed cell | [illegible] | Pore size | Pore density Low | CFD |
|---|---|---|---|---|---|---|---|---|---|
| AM289 | MED | HIGH | [illegible] | LOW | OPEN | MED | HIGH | MED | HIGH |
| AM096 | SLOW | HIGH | [illegible] | LOW | CLOSED | HIGH | LOW | LOW | HIGH |
| AM113 | SLOW | MED | [illegible] | MED | OPEN | LOW | HIGH | MED | LOW |
| AM244 | SLOW | HIGH | [illegible] | LOW | CLOSED | HIGH | LOW | MED | HIGH |
| AM315 | FAST | HIGH | [illegible] | LOW | CLOSED | HIGH | LOW | MED | HIGH |

*Table 3: Characteristics of materials with a high net apposition score.*

FIG. 19C

| Formulation | Cream Kinetics | Expansion | PEG content | H2O Uptake | Open or closed cell | [illegible] | Pore size | Pore density Low | CFD |
|---|---|---|---|---|---|---|---|---|---|
| AM654 | FAST | LOW | PHIL | HIGH | OPEN | MED | HIGH | MED | LOW |
| AM094 | MED | MED | PHIL | HIGH | MOSTLY CLOSED | -- | MED | LOW | LOW |

*Table 4: Characteristics of materials with a low net apposition score.*

FIG.19D

| Formulation | Cream Kinetics | Expansion | PEG content | H2O Uptake | Open or closed cell | [illegible] | Pore size | Pore density Low | CFD |
|---|---|---|---|---|---|---|---|---|---|
| AM062 | MED | HIGH | [illegible] | LOW | OPEN | MED | HIGH | MED | HIGH |
| AM289 | MED | HIGH | [illegible] | LOW | OPEN | MED | HIGH | MED | HIGH |
| AM374 | MED | MED | [illegible] | HIGH | OPEN | LOW | LOW | HIGH | LOW |
| AM096 | SLOW | HIGH | [illegible] | LOW | CLOSED | HIGH | LOW | LOW | HIGH |
| AM113 | SLOW | MED | [illegible] | MED | OPEN | LOW | HIGH | MED | LOW |
| AM244 | SLOW | HIGH | [illegible] | LOW | CLOSED | HIGH | LOW | MED | HIGH |

*Table 5: Characteristics of materials with low blood loss.*

FIG.19E

| Formulation | Cream Kinetics | Expansion | PEG content | H2O Uptake | Open or closed cell | [illegible] | Pore size | Pore density Low | CFD |
|---|---|---|---|---|---|---|---|---|---|
| AM654 | FAST | LOW | PHIL | HIGH | OPEN | MED | HIGH | MED | LOW |
| AM094 | MED | MED | PHIL | HIGH | MOSTLY CLOSED | -- | MED | LOW | LOW |

*Table 6: Characteristics of materials with high blood loss.*

FIG. 19F

| *Polyol phase* | | *Formulation* | | | | | | | | | | |
|---|---|---|---|---|---|---|---|---|---|---|---|---|
| | | *AM062* | *AM096* | *AM113* | *AM201* | *AM289* | *AM315* | *AM374* | *AM474* | *AM735* | *AM746* | *AM880* |
| Polyols | *Poly-G 85-29* | | | 97 | | 97 | | | 30 | | 76 | |
| | *Pluracol 816* | 97 | | | 97 | | 45 | 71 | | 93 | | |
| | *Poly-G 76-120* | | 100 | | | | 40 | 7.1 | 30 | 7.0 | | |
| | *PPG 1200 Da* | | | | | | | | | | | 100 |
| | *TMPEO 1014* | 3.0 | | 3.0 | 3.0 | 3.0 | 15 | 21 | 15 | | 24 | |
| | *UCON 75-H-9500* | | | | | | | | 25 | | | |
| Surfactants | *Tegostab B 4690* | | 1.0 | 1.0 | | | | 0.3 | 0.9 | | | |
| | *Tegostab B 8629* | 1.0 | | | | 2.0 | 2.0 | | | 2.0 | 0.8 | |
| | *Tegostab B 8671* | | | | | | | | | | | 1.0 |
| Amine catalysts | *DABCO 33LV* | 0.8 | | 0.4 | 0.7 | 3.2 | 6.4 | 3.0 | 0.8 | 4.0 | 1.3 | 0.5 |
| | *Niax A1* | 0.1 | 0.6 | 0.2 | 0.1 | 0.3 | | 0.2 | | | 0.2 | |
| | *Diethanolamine* | 1.0 | | 1.0 | | | | | | | 0.5 | |
| Water | *DI water* | 3.6 | 5.5 | 3.6 | 3.7 | 7.2 | 14.4 | 8.0 | 3.6 | 14 | 5.6 | 6.0 |
| Additives | *Stannous Octoate* | | 0.6 | | | | | | | | | 1.0 |
| | *Acetic Acid* | | 1.1 | 0.5 | | | | | 1.2 | 0.5 | 0.5 | |
| | *Ortegol 501* | | | | | | | 0.4 | | | 0.5 | |
| | *Diethylene Glycol* | | | | | | | | | | | 3.0 |
| | *1,4-Butanediol* | | | | 3.0 | 6.0 | | | | | | |
| | *Diethyl malonate* | | | | | | | | | | | 15 |
| | *EO content* | 17.8% | 27.0% | 17.4% | 17.7% | 15.6% | 28.0% | 31.6% | 44.6% | 14.5% | 32.8% | 0.0% |
| | | | | | | | | | | | | |
| Isocyanates | *Mondur MRS-2* | | 109 | 58 | | | 176 | | 48 | | 68 | 154 |
| | *Lupranate M20* | 61 | | | 66 | 123 | | 35 | | 78 | | |

*Table 7:* *Examples of polyurethane foam compositions formed by cross-linking polyols with isocyanates.*

FIG. 19G

IN SITU FORMING HEMOSTATIC FOAM IMPLANTS

CROSS-REFERENCE TO RELATED APPLICATIONS

This application is a continuation of U.S. application Ser. No. 14/928,857, filed Oct. 30, 2015 and titled "In Situ Forming Hemostatic Foam Implants", which is a divisional of U.S. application Ser. No. 13/209,020, filed Aug. 12, 2011 and titled "In Situ Forming Hemostatic Foam Implants", which is a continuation-in-part of U.S. application Ser. No. 12/862,362, filed Aug. 24, 2010 and titled "Systems and Methods Relating to Polymer Foams", which claims priority to U.S. Provisional Patent Application Ser. No. 61/236,314 filed Aug. 24, 2009, titled "Systems and Methods Relating to Polymer Foams", and U.S. Provisional Patent Application Ser. No. 61/368,095 filed Jul. 27, 2010, titled "Fiber Composite Structure", which are incorporated by reference herein for all purposes.

FIELD OF INVENTION

Systems and methods relating to polymer foams are generally described.

BACKGROUND

Early stabilization of body fluid loss can be important in the treatment of wounds. For example, many injuries are treatable if effective hemorrhage control and operative surgical intervention are undertaken rapidly. However, in many situations, immediate access to surgical care is not available. Internal wounds may be particularly difficult to treat in such situations, as traditional treatment techniques (e.g., application of pressure to stop bleeding, etc.) are difficult to implement with such wounds.

The use of polymers in the treatment of wounds is well known in the art. However, previous materials and methods for treating wounds with polymers have suffered from a variety of drawbacks. For example, many polymers irritate skin and/or internal tissues, or are not sufficiently biodegradable to be suitable for use inside a body cavity. Moreover, many polymers also lack suitable mechanical properties to be useful inside the body; polymers that are too stiff may lead to discomfort or further injury, while polymers that are too soft may fail to provide adequate support for internal tissues.

Finally, polymers can be difficult to place within a body cavity.

SUMMARY OF THE INVENTION

Systems and methods relating to polymer foams are provided. The subject matter of the present invention involves, in some cases, interrelated products, alternative solutions to a particular problem, and/or a plurality of different uses of one or more systems and/or articles.

In one aspect, the present invention comprises a method comprising the introduction of a flowable polymer formulation into a body cavity, foaming the polymer formulation within the body cavity to produce an elastomeric polymer foam, and preventing or limiting bleeding within the body cavity, relative to an amount of bleeding that would occur under essentially identical conditions in the absence of the elastomeric polymer foam.

In certain embodiments, the method comprises a method comprising cross-linking a condensation polymer of a polyol and a polyacid within a body cavity, foaming the condensation polymer within the body cavity to produce an elastomeric polymer foam, and preventing or limiting movement of a bodily fluid within the body cavity, relative to an amount of movement of bodily fluid that would occur under essentially identical conditions in the absence of the elastomeric polymer foam.

In certain embodiments, the present invention comprises a method comprising the injection of a flowable polyol and polyisocyanate mixture into a body cavity, foaming the polymer formulation within the body cavity to produce an elastomeric polymer foam, and preventing or limiting bleeding within the body cavity, relative to an amount of bleeding that would occur under essentially identical conditions in the absence of the elastomeric polymer foam.

In another aspect, the present invention comprises a method of forming a foam within a body cavity by introducing a two part formulation into a body cavity, foaming the formulation, cross-linking the formulation, and preventing or limiting movement of a bodily fluid within the body cavity, relative to an amount of movement of a bodily fluid that would occur under essentially identical conditions in the absence of the foam. In certain embodiments, the formulation and/or the foam can have physical characteristics that are advantageous for preventing or limiting the movement of a bodily fluid, including hydrophilicity, hydrophobicity, hygroscopy or miscibility with water, the degree of expansion of the foam, the density of the foam, the softness of the foam, the viscosity of the formulation, and the kinetics of form formation from the formulation.

In another aspect, the present invention comprises a method comprising placing a polymer foam between two tissues to prevent tissue adhesion.

In other aspects, the invention includes foams, compositions, formulations, products, kits, and systems that are useful for performing the methods described above.

The present invention offers advantages not previously known in the art. For example, the polymers of the invention can be deployed into a closed body cavity without requiring specific knowledge of injury site(s) while nonetheless creating conformal contact with actively bleeding injuries located throughout the cavity. Other advantages and novel features of the present invention will become apparent from the following detailed description of various non-limiting embodiments of the invention when considered in conjunction with the accompanying figures. In cases where the present specification and a document incorporated by reference include conflicting and/or inconsistent disclosure, the present specification shall control. If two or more documents incorporated by reference include conflicting and/or inconsistent disclosure with respect to each other, then the document having the later effective date shall control.

BRIEF DESCRIPTION OF THE DRAWINGS

Non-limiting embodiments of the present invention will be described by way of example with reference to the accompanying figures, which are schematic and are not intended to be drawn to scale. In the figures, each identical or nearly identical component illustrated is typically represented by a single numeral. For purposes of clarity, not every component is labeled in every figure, nor is every component of each embodiment of the invention shown where illustration is not necessary to allow those of ordinary skill in the art to understand the invention. In the figures:

FIG. 19A-G are tables showing various embodiments of the invention. FIG. 19A is a table showing the semi-quantitative scoring system that was developed for an assay to evaluate transport of the formulations. FIG. 19B is a table summarizing the performance of certain formulations in the in vivo transport assay and includes a "Net apposition score" for each formulation. FIG. 19C is a table showing the characteristics of high-scoring formulations. FIG. 19D is a table showing the characteristics of low-scoring formulations. FIG. 19E is a table showing characteristics of foams exhibiting low blood loss. FIG. 19F is a table showing characteristics of foams exhibiting low blood loss. FIG. 19G is a table showing examples of polyurethane foam compositions formed by cross-linking polyols with multifunctional isocyanates.

DETAILED DESCRIPTION

Figures 1A, 1B, 1C:
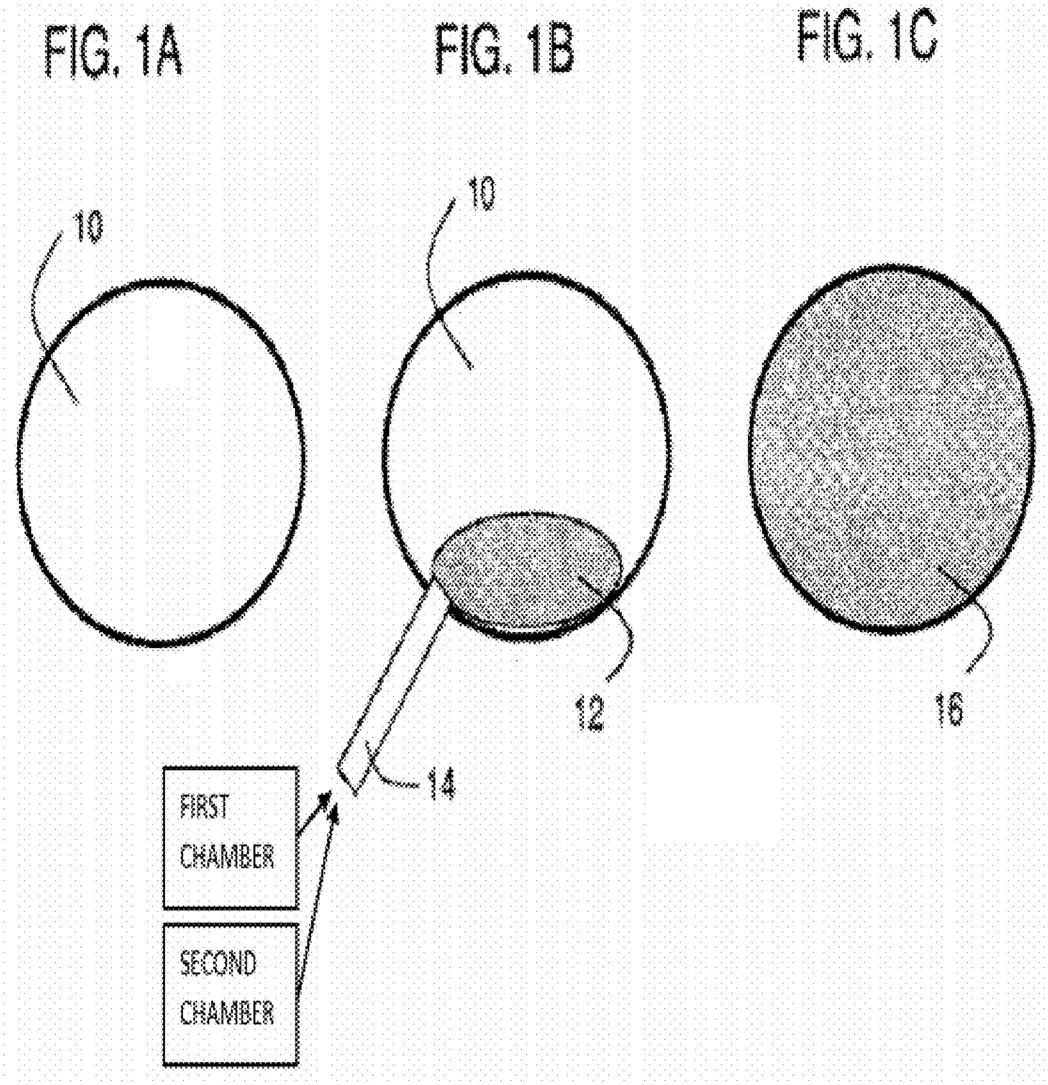
FIGS. 1 A-1 C include schematic illustrations of the formation of a polymer foam, according to one set of embodiments.

Systems and methods related to polymer foams are generally described. Some embodiments relate to compositions and methods for the preparation of polymer foams, and methods for using the polymer foams. The polymer foams can be applied to a body cavity (including, but not limited to the abdominal, pelvic, and cardio thoracic cavities) and placed in contact with, for example, tissue, injured tissue, internal organs, etc. In some embodiments, the polymer foams can be formed within a body cavity (i.e., in situ foam formation). In addition, the foamed polymers may be capable of exerting a pressure on an internal surface of a body cavity and preventing or limiting movement of a bodily fluid (e.g., blood, etc.). Foams of the invention can be used to treat incompressible hemorrhage from wound sites that are unknown or unable to be visualized within potentially tortuous body cavities. Certain compositions of the invention can be deposited within a body cavity and reacted to form polymer foams within or proximal to a wound site, which foams may apply pressure to or limit fluid flow from the wound site. Alternatively, compositions of the invention can be deposited distal from a wound site to create a foam that expands in volume to fill a body cavity, achieving close apposition to a wound and thereby applying pressure thereto or limiting the flow of fluids therefrom.

The polymer foams may possess attributes that make them particularly suitable for use within the body. For example, in some embodiments, the polymers used to form the foams described herein may be biocompatible. The polymers may also be biodegradable in some cases. In some instances, the polymers may be sufficiently elastic to allow for body movement while being sufficiently stiff to support body tissues. In some embodiments, the composition of the polymer may be adjusted so that it wets tissues effectively. Furthermore, pendant groups may be attached that allow for the targeted adhesion of polymer to tissues or injured tissues. Functionalization of the polymer used to form the foam may also lead to covalent bonding of the foam to a surface inside the body cavity, which may aid, for example, in preventing dislocation of the foam within the cavity.

The materials and methods described herein exhibit several advantages relative to traditional wound treatment methods. For example, some embodiments described herein allow for the delivery of polymer directly to, and permeation throughout, a body cavity. The viscosity and wetting properties of the polymers can be tailored such that the polymers are easily injected into a wound cavity, forming, in some cases, a rapidly expanding elastomeric foam that fills the body cavity, coats one or more tissue surfaces, and/or cross-links within the body cavity. In addition, the polymers may comprise entities that allow for the degradation of the polymer foam via an external stimulus such as UV radiation, heat, etc. The polymers and/or foams formed therefrom may also be capable of interacting with contrast agents, allowing for the visualization of a body cavity.

Additional advantages of the polymer foams described herein are described in more detail below.

Polymer foams may be used in a variety of applications. In some embodiments, the polymer foams may be used to provide support to and/or stabilize bodily fluid loss from organs (e.g., the liver, spleen, etc.). Such use may be advantageous in treating organs or tissues that are damaged, for example, in blunt trauma injuries. The polymer foams may also be used to fill a body cavity created by the loss of body tissue. As used herein, "body cavity" refers to any space located within a body including spaces within the external surface of the skin. It should be noted that body cavities may be, in some cases, exposed to the external environment surrounding a body, such as, for example, in the case of an open wound or surgical incision. In some embodiments, polymer foams may be formed or located within an enclosed body cavity, for example, by placing a polymer in the body cavity and closing an incision such that the polymer or polymer foam are not exposed to the external environment. While the embodiments described herein may find particularly advantageous use within body cavities, the use of the polymer foams are not limited to body cavities, and may be used, for example, to treat burns and other external wounds.

Examples of polymer foams and methods associated therewith are now provided. In particular, systems and methods for foaming a polymer to form a polymer foam are now described in connection with one set of embodiments. FIGS. IA-IC include schematic illustrations of the formation of a polymer foam within a body cavity. As used herein, a "polymer foam" refers to an article comprising a plurality of cells (i.e. volumes) that are at least partially surrounded by a material comprising a polymer. The cells within the foam may be open or closed. The cells within the foam may be any suitable size. In some embodiments, the polymer foam may comprise at least I0 cells, at least I00 cells, at least I000 cells, at least I0,000 cells, or more.

FIG. 1 A includes body cavity 10 in which a polymer foam can be formed. In FIG. 1 B, polymer material I2 is provided to cavity 10 via source I4. The polymer material can comprise a plurality of polymers which can be, for example, cross-linked to each other in the process of forming a polymer foam. In some embodiments, the polymer material comprises fluid polymers in the substantial absence of a carrier fluid. In other instances, the plurality of polymers in the polymer material are suspended in a carrier fluid (e.g., a liquid suspension medium, etc.). The term "polymer" is given its ordinary meaning in the art, and is used to refer to a molecule that includes a plurality of monomers. In some embodiments, a polymer may comprise fewer than about 100, fewer than about 50, fewer than about 25, or fewer than about 10 monomer units. In some embodiments, a polymer may comprise between about 2 and about 100, between about 2 and about 50, between about 2 and about 25, between about 5 and about 50, or between about 5 and about 25 monomer units. The polymers within the polymer material can comprise a variety of functional groups that allow the polymers to, for example, cross-link to each other, attach to tissue or other material within the body cavity, interact with agents in the bloodstream of the subject (e.g., imaging agents, cross-linking agents, etc.), among other functionalities.

Source 14 may comprise any suitable source known to one of ordinary skilled in the art. In some embodiments, source 14 comprises any suitable container through which polymer material 12 may be passed. For example, in some embodiments, the source may comprise a syringe having one or more barrels through which the polymer material is flowed. In some embodiments, the source may comprise a container in which the polymer material is under pressure, and the polymer material is released from the container upon depressurizing the container (e.g., as in an aerosol can). In such embodiments, the polymer material can be applied as a spray, for example. The container may comprise several means for pressurizing known to those of ordinary skill in the art. For example, the container may be pressurized during the filling process in a manufacturing environment, or pressure may be generated immediately prior to use. In one embodiment, one or more pressure-generating chemical reactions may occur within the container, with the user initiating the reaction, waiting for pressure build-up and releasing the material. In another embodiment, pressure may be generated manually, via hand pump, crank, or rotary device. The container may also have an attachment that is introduced into the body that allows the material to flow into the cavity such as a Veress needle or nozzle or other means known to those of ordinary skill in the art. The openings on the introducer tip can be multidirectional in order to distribute the polymer in all directions within the cavity. That attachment or introducer may be rigid, soft, straight, flexible or conformable to a tortuous path. The introducer may have various tips for easy entry into the abdominal cavity through the tough abdominal wall and muscles. It may also have a flexible or retractable tip that will protect organs, intestines, bowels from perforations. It may be shaped to be non-coring and atraumatic. A surface finish or coating such as PTFE or silicone may be applied to part of or all of the introducer to make it lubricious and easy to introduce into the body. Additionally, a surface finish or coating can be applied to part or all of the introducer to make it remain in position once it is introduced. The surface finish or coating can be directional, allowing easy insertion but difficult removal.

Figure 2A:
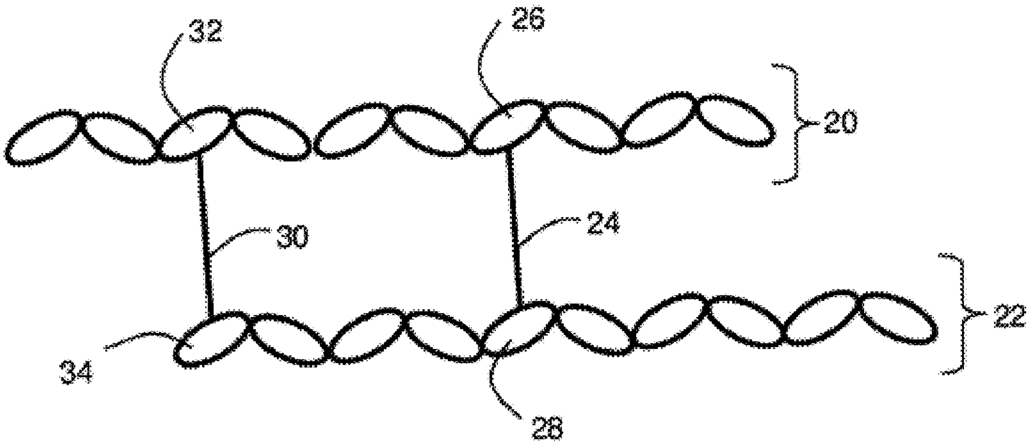
FIGS. 2A-2B include exemplary schematic illustrations of cross-linking of polymers.
Figure 2B:
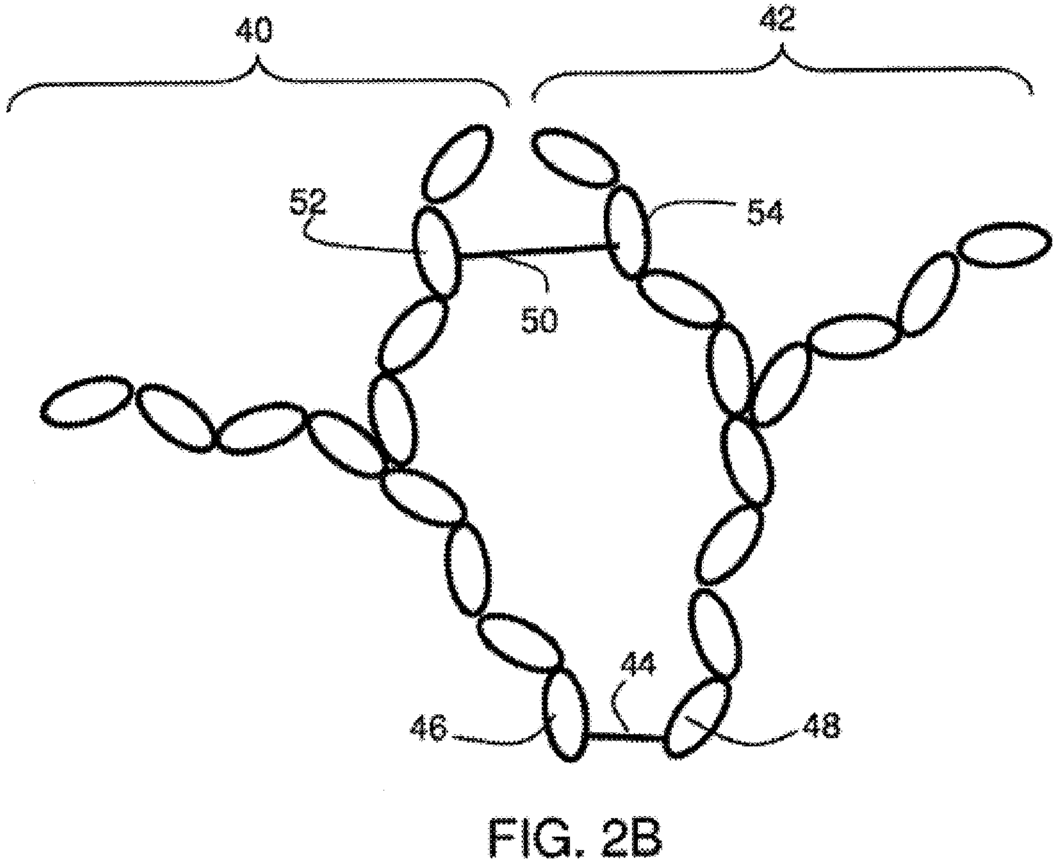

In some embodiments, the polymers within the polymer material may cross-link within the body cavity. The term "cross-linking" is used to refer to the process whereby a pendant group on a first polymer chain may react with a second polymer chain (e.g., a pendant group on the second polymer) or other molecule or molecules to form a covalent or ionic bond joining the two polymers. Polymers that can undergo cross-linking can comprise straight chains, branched chains having one or more arms (i.e., multi-arm chains), or mixtures of these. In some cases, the polymer (branched and/or non-branched) may contain reactive side chains and/or reactive terminal groups (i.e., groups at the end of a polymer chain), and cross-linking may involve reactions between the side chains, between terminal groups, and/or between a side chain and a terminal group. For example, in FIG. 2A, polymers 20 and 22 are cross-linked, with bond 24 (which may comprise a single covalent bond or a plurality of covalent bonds between multiple atoms) between monomer 26 and monomer 28. In addition, bond 30 is formed between non-terminal monomer 32 and terminal monomer 34. In FIG. 2B, branched polymers 40 and 42 are cross-linked, with bond 44 between monomer 46 and terminal monomer 48, and bond 50 between monomers 52 and 54. In some instances, the polymer material may be substantially free of polymers that comprise reactive groups on terminal monomers. In other cases, the polymer material may comprise a substantial amount of polymers with reactive groups on terminal monomers. In some embodiments (e.g., in some cases in which branched polymers are employed) a relatively large percentage of the cross-linking reactions (e.g., at least about 70%, at least about 80%, at least about 90%, at least about 95%, at least about 99%, or substantially all of the cross-linking reactions) can occur between terminal reactive groups.

Cross-linking may commence via a variety of mechanisms. In some embodiments, polymer may cross-link once the polymer contacts moisture (e.g., water, blood, aqueous solutions, etc.), for example, within a body cavity. Cross-linking may be achieved via acrylate, methacrylate, vinyl, cinnamic acid, or acrylamide groups in some embodiments. Such groups may be cross-linked via the application of ultraviolet radiation and can be used in conjunction with an external foaming agent. In some instances, a cross-linking initiator may be introduced into the subject in which the body cavity is located (e.g., via the bloodstream, via a separate container in the delivery system such that the initiator and the polymer do not mix before delivery, etc.) to initiate cross-linking of the polymer. For example, a free radical initiator, such as eosin or 2,2-dimethoxy-2-phenylacetophenone, can be used to initiate cross-linking of polymers bearing acrylate, methacrylate, or vinyl groups. Other examples of reactive groups on polymer chains that can be paired to produce cross-linking include, but are not limited to, hydroxyls and isocyanates, amines and NHS-esters, thiols and maleimides, azides and alkynes (i.e. "click chemistry"), acid chlorides and alcohols, and in a preferred embodiment, isocyanates and polyols. It may be desirable, in some embodiments, to keep these paired chemicals separate until they are introduced into the body cavity to prevent unwanted cross-linking outside the body cavity. For example, the polymer may include azide functional groups, and alkynes can be introduced to the body cavity from a container separate from the container used to introduce the polymer. In some embodiments, these chemistries are also employed in conjunction with an external foaming agent. As the polymer material cross-links, its viscosity may be increased. In some cases, the cross-linking proceeds until a substantially solid material (e.g., a solid elastomeric foam) is formed.

Referring back to the example in FIG. I, polymer material I2 (and/or a cross linked or partially cross-linked product of the polymer material) is foamed to form polymer foam I 6, as illustrated in FIG. IC. The foam may be formed, for example, by introducing a gas into the polymer material. Once the gas is supplied to the polymer, the gas may be dispersed within the polymer (e.g., as bubbles) to form the cells of the foam. The dispersion of gas within the polymer may lead to expansion of the polymer such that it substantially fills the body cavity, as shown in FIG. IC. In some cases, the foaming step may involve self-expansion of the polymer, for example, when gas is generated by a hydrolysis reaction or as a byproduct of a reaction between functional groups on different polymer chains. Thus, cross-linking and foaming may take place substantially simultaneously in some embodiments. The self-expansion of the foam may drive the polymer into interstitial regions of the body cavity that otherwise may be difficult to reach. In addition, the self-expanding foam may provide internal compression against the walls of the body cavity.

In some embodiments, the foaming step is not dependent upon the cross-linking step to form a foaming gas. For example, the foaming step may occur due to an introduction of gas separate from the polymer material. In some cases, gases comprising air, $CO_2$, or other materials may be introduced into the body cavity via an external source (e.g., a syringe or any other suitable container). This gas may then permeate the polymer material (or a cross-linked product) to form bubbles within the material, which may form the voids in the foam as polymeric material cross-links around them. In cases where the gas is supplied via an external source, the source of the gas may be the same as or different from the source of the polymer material (e.g., 14 in FIG. 1).

In some embodiments, the gas may be supplied as a product of a chemical reaction of part of the polymer or a cross-linked product. For example, in some embodiments, the foaming step comprises reacting one or more pendant groups on the polymer or cross-linked product to form a gaseous product. The gas-producing pendant groups may react upon contact with another material in the body cavity. For example, in some cases, the gas producing groups may react upon contact with moisture in the body cavity. In some cases, the gas-producing pendant groups may react with a chemical supplied to the body cavity separately from the polymer material (e.g., via the bloodstream, via an external source separate from the polymer material source, etc.). In some embodiments, the gas-producing pendant groups on the polymer chain may react with another component that is supplied to the body cavity. In some embodiments, the polymer or cross-linked product may comprise $CO_2$-producing groups. Examples of $CO_2$-producing groups include, but are not limited to, isocyanate groups, carbonates, bicarbonates, and carbamates. Such groups may produce $CO_2$ gas when reacted with an acid, for example. In some cases, the $CO_2$-producing group may include an N-hydroxysuccinimide carbonate, illustrated below:

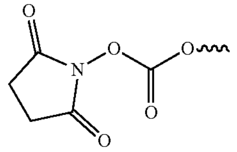

$CO_2$-producing groups may include, in some cases, imidazole carbamates, as illustrated below:

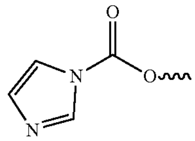

As noted above, in some embodiments, the foaming and cross-linking steps occur substantially simultaneously. In some cases, the foaming and cross-linking steps may occur substantially simultaneously, but remain independent of each other. For example, the polymer material may cross-link by reacting with water in the body cavity, and, at substantially the same time, gas may be introduced to the polymer material from an external container. In another embodiment, a first material containing gas generating groups may produce gas by contact with a second agent (e.g., water in the body, water supplied separately, or chemical additive), while contact or interaction with a third material leads to crosslinking. For example, at the time of delivery, polymer A with isocyanate groups can be mixed with water and polymer B, in which the former causes the generation carbon dioxide to foam the material and polymer B can contain hydroxyl groups that react with isocyanates on polymer A to form a cross linked network between polymers A and B.

The foaming and cross-linking steps may be, in some cases, part of the same reaction process. For example, one or more reactions may produce a gaseous by-product which serves as the supply of gas to form the polymer foam, but concurrently leads to the generation of new functional groups that enable crosslinking. The gaseous by-product can be trapped within the polymer and coalesce to form bubbles. As the reaction progresses, the formation, growth and expansion of the gas bubbles can expand the polymer volume and force it into interstitial areas of the body cavity. As the polymer cross-links, a three-dimensional foam can be formed within the body cavity. The volume expansion and cross-linking can serve to coat and seal surfaces of the body cavity, and optionally provide internal compression, which may be useful, for example, in stopping bleeding. In addition, such a reaction scheme can be combined with an external supply of gas (e.g., $CO_2$ in an external container) to increase the amount of gas contained in the polymer or a cross-linked product of the polymer.

Figure 3:
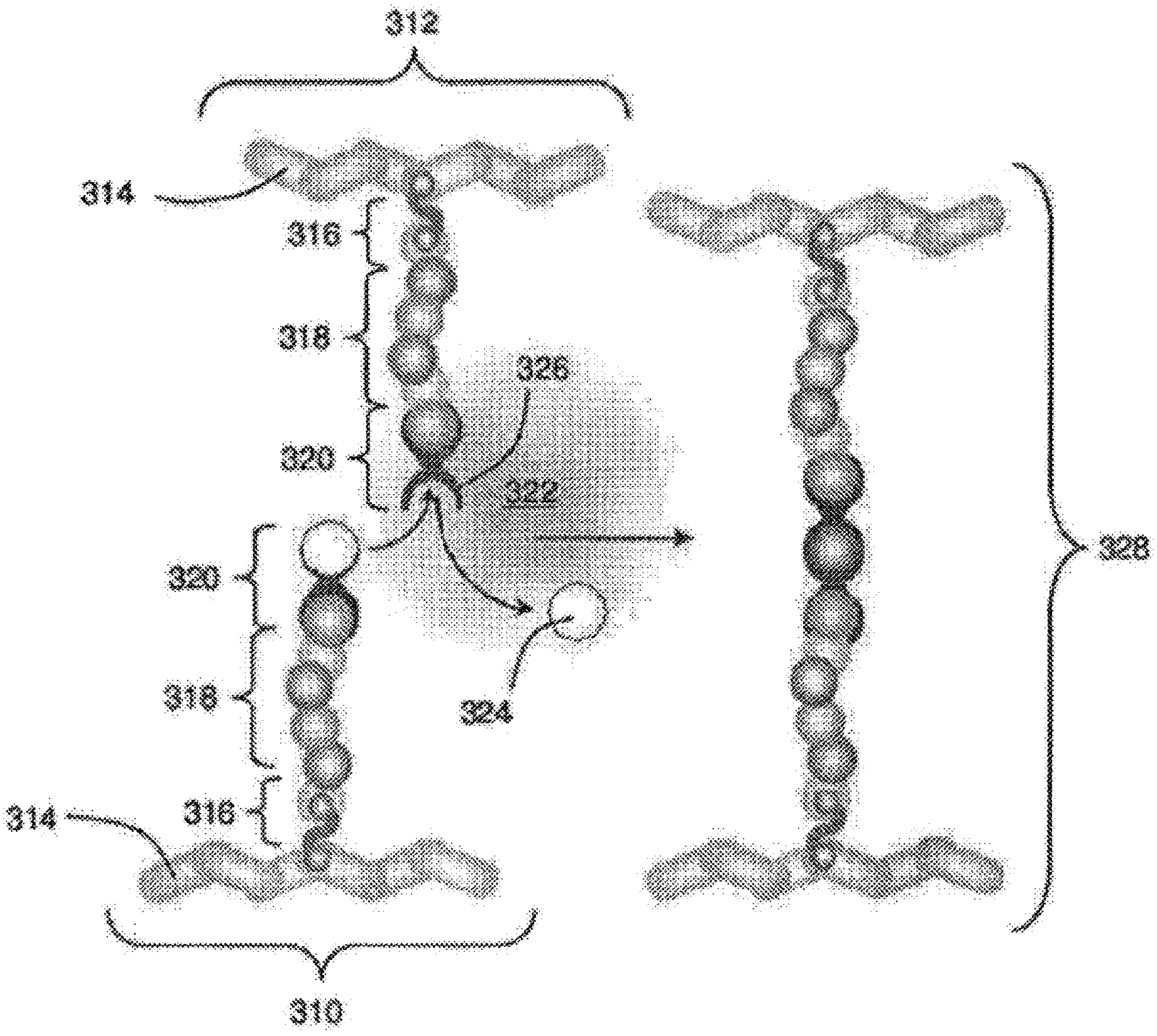
FIG. 3 includes a schematic illustration of cross-linking and gas generation, according to one set of embodiments.

FIG. 3 includes an exemplary schematic diagram of a system in which simultaneous cross-linking and gas generation occur. Polymers 310 and 312 include biodegradable backbones 314. The polymer may also comprise a linker region 316 to attach pendant groups. The polymer may also comprise a targeting ligand 318 which can be used to bond the polymer to desired sites (e.g., damaged tissue). In addition, the polymer in FIG. 3 includes a cross-linking site 320 that can simultaneously solidify and foam the material. When the polymer is exposed to a compound 322 (e.g., water) in the body cavity, gas 324 is released from the cross-linking site, which generates a functional group 326 that can react with another polymer to produce a cross-linked structure 328.

All of the foaming mechanisms described herein may occur before any substantial cross-linking has occurred or during cross-linking of the polymer material or a cross-linked product of the polymer material. For example, in some cases, an external gas may be introduced into and dispersed within a polymer material that has not substantially cross-linked. The polymer material may then cross-link around the bubbles to form the foam. In such cases, the viscosity of the polymer material can be chosen such that the material is able to retain bubbles within the volume without the need for cross-linking. In some embodiments, at least some cross-linking may occur before the gas is introduced to the polymer material, and the gas is dispersed within a partially cross-linked polymer material that has not completely solidified to form a foam.

Cross-linking and/or foaming may be achieved, in some instances, using isocyanate chemistry. Isocyanate groups are relatively unstable when exposed to water and moisture. Exposure of isocyanate groups to water or moisture (or other compounds) can lead to the decomposition of the groups, cross-linking of polymers to which they are attached, and release of carbon dioxide, as shown below for a model lysine isocyanate:

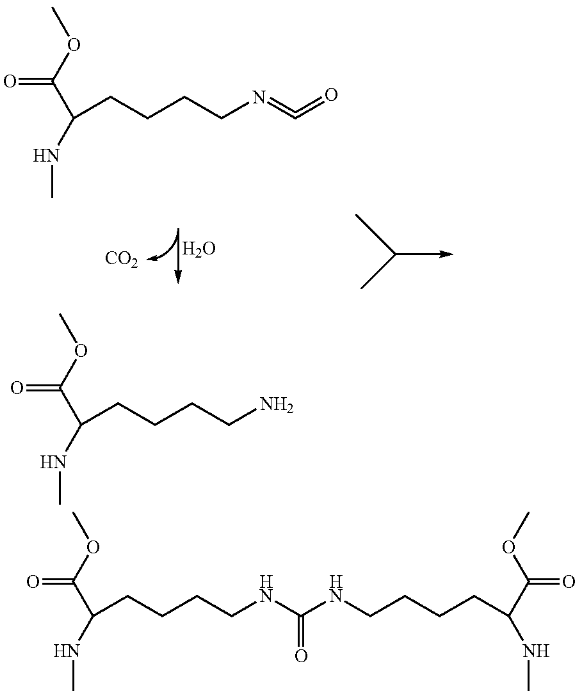

In the mechanism above, the isocyanate is partially hydrolyzed to produce amines, which can react with native, non-hydrolyzed isocyanates, as shown above. Not wishing to be bound by any theory, a cross-linked structure can be produced because the rate of the amine-isocyanate reaction may be on the order of or faster than the rate of isocyanate hydrolysis, and inter-chain reactions occur between these functional groups to ultimately form a cross-linked structure. The isocyanates on the polymer can also react with amine groups of the tissue (e.g. lysines in proteins), which can form a covalent bond with the tissue to further strengthen the seal at sites in which fluid is being lost (e.g., at bleeding sites). In addition, the isocyanate hydrolysis reaction produces $CO_2$, enabling simultaneous cross-linking and gas production in a single-reaction scheme.

In certain embodiments, polyurethane foams may be generated by cross-linking polyols with multifunctional isocyanates. Polyols suitable for use in such embodiments include polyether- and polybutadiene-based polyols. Polyols of particular interest include polypropylene glycol (PPG) and polyethylene glycol (PEG), as well as random and block copolymers thereof. Also suitable for use are polycarbonates, polybutadienes, and polyesters. Diols, triols, and tetrols are most preferred, but multifunctional polyols with any suitable number of arms may be used. Molecular weights between 100 and 10,000 Da are preferable, with molecular weights up to 6,000 Da being most preferred, and blends of polymers with different molecular weights, degrees of branching, and composition are often used. Commercial polymers of particular interest include polypropylene glycols (425, 1200 Da), polyethylene glycols (200, 400, 600, 1000, 2000, 3000 Da), Pluracol products (355, 1135i, 726, 816), Arch Poly-G 30-240, Poly-G 76-120, Poly-G 85-29, trimethylolpropane ethoxylate (450, 1014 Da), pentaerythritol ethoxylate (797 Da), UCON 75-H-1400, UCON 75-H-9500, dipropylene glycol, diethylene glycol, tripropylene glycol, triethylene glycol, tetrapropylene glycol, and tetraethylene glycol. In preferred embodiments, polyols used in the present invention have a polyethylene oxide content of 0-50 wt %, more preferably 0-40 wt %, more preferably 0-30 wt %, more preferably 0-25 wt %, and most preferably 0-16.5 wt %. Also preferred is that polyols used in the present invention comprise an amine catalyst in an amount up to 10 pphp, a water content of up to 20 pphp, a surfactant in an amount up to 10 pphp, and a diluent up to 300 pphp (preferably up to 250 pphp and most preferably up to 15 pphp). Examples polyurethane foams generated by cross-linking polyols with multifunctional isocyanates, in accordance with the present invention, are listed in Table 7.

Isocyanates suitable for use in such embodiments include any polymeric isocyanate with a degree of functionality greater than 2.0, with the most useful range being 2.0-2.7. Preferred polymeric isocyanates are based on methylene diphenyl isocuanate (MDI). Isocyanate true-prepolymers and quasi-prepolymers may also be used. In this case, a "quasi-" prepolymer, or semi-prepolymer, is a polymer formed by the reaction between a multifunctional isocyanate and polyol, where the isocyanate-to-alcohol ratio is greater than the stoichiometric two-to-one ratio. A "true-" prepolymer, or strict-prepolymer, is a polymer formed by the reaction between a multifunctional isocyanate and polyol, where the isocyanate-to-alcohol ratio is equal to the stoichiometric two-to-one ratio.

In some instances, it may be advantageous to position isocyanate groups in the polymer so that it is accessible for hydrolysis and cross-linking, without inhibiting binding to the tissue (e.g., damaged blood vessels). In one set of embodiments, a lysine group in the targeting peptide can be converted to an isocyanate by reaction with diphosgene. In some instances, the isocyanate and peptide chemistries can be completely decoupled by modifying a fraction of the side chains with peptide while the balance are modified with isocyanate.

The polymer that is foamed to form the polymer foams described herein may be formed using a variety of chemistries. In some embodiments, the polymer comprises a synthetic polymer. As used herein, a “synthetic polymer” refers to a polymer that is a product of a reaction directed by human interaction. For example, synthetic polymers can include polymers synthesized by reactions of natural or synthetic monomers or combinations thereof that are directed by human interaction. The formation of synthetic polymers can also include chain elongation of natural or synthetic polymers. In some embodiments, the synthetic polymer is not found in nature. In other cases, the synthetic polymer can be found in nature, but the polymer is synthesized via human interaction (e.g., in a laboratory setting). In some embodiments, the polymer may comprise a poly alpha-hydroxy acid. In some cases, the polymer may comprise a polyester. In some cases, the polymer may comprise a polyether-polyester block copolymer. In some cases, the polymer may comprise a poly (trimethlyene carbonate). In some embodiments, the backbone of the polymer can exclude at least one of polynucleotides, proteins, and polysaccharides.

In some embodiments, the polymer foam is formed by cross-linking a condensation polymer of a polyol and a polyacid. The terms “polyol” and “polyacid” are given their standard meanings in the art, and are used to refer to compounds comprising at least two alcohol groups and at least two acidic groups, respectively. Examples of polyols suitable for use in forming the condensation polymer used to form the polymer foams described herein include, but are not limited to, glycerol, polyethylene glycol, polypropylene glycol, polycaprolactone, vitamin B6, erythritol, threitol, ribitol, arabinitol, xylitol, allitol, altritol, galactritol, sorbitol, mannitol, iditol, lactitol, isomalt, and maltitol, wherein the functional groups present on the polyol are optionally substituted. Examples of polyacids suitable for use in forming the condensation polymer used to form the polymer foams described herein include, but are not limited to, succinic acid, fumaric acid, a-ketoglutaric acid, oxaloacetic acid, malic acid, oxalosuccinic acid, isocitric acid, cis-aconitic acid, citric acid, 2-hydroxy-malonic acid, tartaric acid, ribaric acid, arabanaric acid, xylaric acid, allaric acid, altraric acid, galacteric acid, glucaric acid, mannaric acid, dimercaptosuccinic acid, oxalic acid, malonic acid, succinic acid, glutaric acid, adipic acid, pimelic acid, suberic acid, azelaic acid, sebacic acid, malic acid, or vitamin BS, wherein the functional groups present on the polyacid are optionally substituted.

In some embodiments, the condensation polymer may comprise poly (glycerol-sebacate) (PGS). An exemplary synthesis pathway in which glycerol and sebacic acid are used to form PGS is shown below:

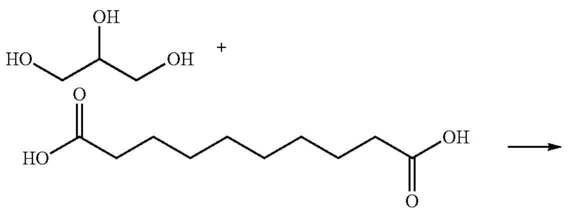

-continued

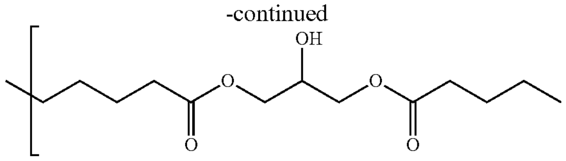

In some embodiments, the polymer foam is formed by cross-linking a polymer comprising the following formula (I):

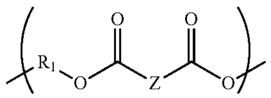

(I)

wherein RI and Z can be the same or different and each is an alkyl, heteroalkyl, alkenyl, heteroalkenyl, alkynyl, heteroalkynyl, aryl, heteroaryl, heterocycle, acyl or carbonyl group, any of which may be optionally substituted, and wherein n is an integer greater than I. In some embodiments, RI and/or Z are substituted with a gas producing group. For example, RI and/or Z may be substituted with a C02-producing group (e.g., isocyanate).

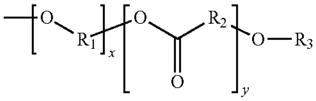

(II)

wherein $R_1$ and $R_2$ can be the same or different and each is an alkyl, heteroalkyl, alkenyl, heteroalkenyl, alkynyl, heteroalkynyl, aryl, heteroaryl, heterocycle, acyl or carbonyl group, any of which may be optionally substituted; wherein x and y are non-negative integers; wherein RJ may be a hydrogen, gas generating functional group, or tissue binding domain.

In some embodiments, the polymer may comprise the poly (lactic acid) (PLA), poly (glycolic acid) (PGA), and polycaprolactone (PCL) class of polymers and their copolymers, such as poly (lactate-co-caprolactone) or poly (glycolate-caprolactone). Copolymerization of the lactide, glycolide and caprolactone monomers in various ratios can yield materials with a wide range of mechanical properties, thermal characteristics and degradation times. The structure of the PLA/PGA/PCL copolymers (and associated properties such as molecular weight, etc.) can be tailored, in some cases, by adjusting the type of initiator used and its molar ratio with the monomer(s).

In some embodiments, the polymer comprises poly (glycolate caprolactone). In some cases, the PGCL composition includes a ratio of glycolide to caprolactone of about 50:50. An exemplary synthesis pathway for PGCL is shown below, in which pentaerythritol is used as an initiator to form 4-armed, branched structures.

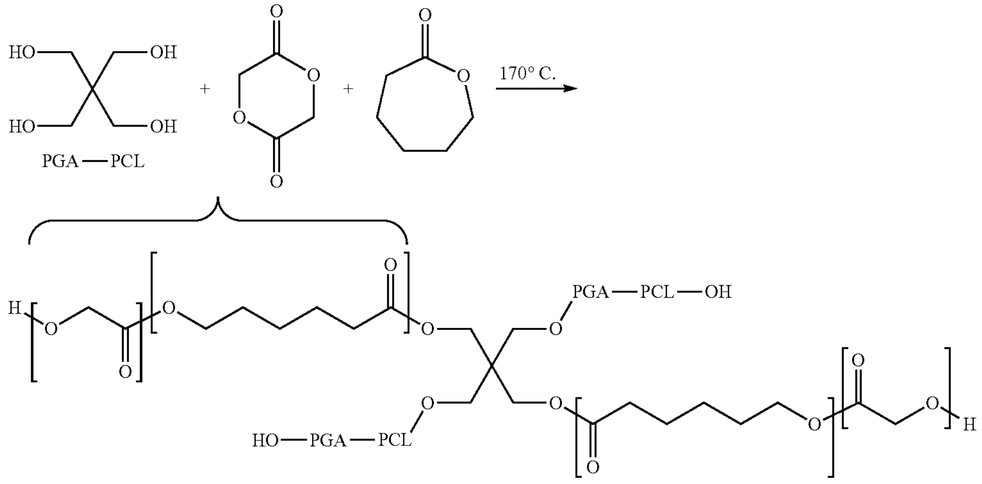

The properties of the polymer used to form the polymer foam may be tailored to achieve a desired result. For example, in some embodiments, the viscosity of the polymer is tailored such that the polymer is able to permeate the body cavity and create conformal contact. An overly viscous polymer may require excessive pressure to deploy within the body cavity. In addition, an overly viscous polymer may inhibit the polymer from accessing interstitial spaces. An overly low-viscosity polymer might be difficult to contain the material to the injured site or may be displaced by the flow of a bodily fluid. One of ordinary skill in the art will be able to produce the desired viscosity for a given polymer type by, for example, adjusting the molecular weight of the polymer. In some embodiments, the viscosity and the molecular weight are related through a power law. The molecular weight of a polymer may be adjusted by, for example, controlling the time of the polymerization reaction used to generate the polymer. In some embodiments, the molecular weight of the polymer is between about 1000 and about 10,000 g/mol or between about 1200 and 6000 g/mol. The viscosity of a polymer may be adjusted by, for example, adding diluents such as any suitable low molecular weight, low viscosity compound, examples of which include triacetin, propylene carbonate, tetraethylene glycol dimethyl ether, dimethyl esters of diacids (e.g., diethyl malonate, dimethyl adipate), dimethyl sulfoxide, and oils (vegetable, olive, castor, etc.). In embodiments that include polyols, it is preferable to add up to about 300 pphp of diluent to control polymer viscosity.

In some embodiments, the polymer is amorphous or semi-crystalline with a glass transition temperature ($T_g$) below room temperature. Such properties yield, in some cases, polymers with sufficiently low viscosities that they can be dispensed from an external container via pressure-driven flow.

In some embodiments, properties or composition of the polymer may be chosen to achieve a desired hydrophilicity or hydrophobicity. The hydrophilicity of the polymer may be selected, in some instances, such that the surfaces (e.g., tissue surfaces) within a body cavity are appropriately wetted. Generally, a material with increased hydrophilicity will have a greater tendency to wet soft tissues surfaces. However, the polymer and resulting polymer foam may be, in some cases, somewhat hydrophobic such that they do not dissolve into biological fluids. Appropriately hydrophilic polymers are capable of conformally wetting interior surfaces of a body cavity while remaining contained within the cavity. In some embodiments, the composition of the polymer may be selected to achieve a desired hydrophilicity. For example, in some embodiments, the chain length of a monomer used to synthesize the polymer can be varied to change hydrophilicity. As a specific example, the carbon chain length between carbonyl groups of a diacid monomer can be varied from between two and eight aliphatic carbons, producing a range of hydrophilicity in the resulting polymer.

In some embodiments, the polymer foams described herein may have favorable mechanical properties. In some embodiments, the polymer foams are elastomeric. The term "elastomer" as used herein, refers to a polymer that can return to the approximate shape from which it has been substantially distorted by an applied stress. In some cases, the elastomeric polymer foams described herein may comprise a polymer having a bulk modulus of between about 0.05 MPa and about 10 MPa; 0.05 MPa and about 100 MPa; and 0.05 MPa and about 500 MPa. Elastomeric polymers may be particularly suitable for use in making polymer foams because they are capable sustaining stress without permanently deforming, while providing adequate support for body organs and tissues.

The time required to form the polymer foam after exposure to the body cavity and the final mechanical and physicochemical properties of the polymer foam can depend on such factors as the composition of the polymer, the density of pendant groups (e.g., cross-linking groups), and relative positions of the pendant groups (e.g., cross-linking groups). One of ordinary skill in the art will be capable of adjusting the concentration and location of pendant groups to produce polymer foams with desirable physical properties.

In some embodiments, the polymer or polymer foam may be biodegradable. As used herein, "biodegradable" describes materials that are capable of degrading down to oligomeric or monomeric species under physiological or endosomal conditions. The phrase "physiological conditions," as used herein, relates to the range of chemical (e.g., pH, ionic strength) and biochemical (e.g., enzyme concentrations) conditions likely to be encountered in the intracellular and extracellular fluids of tissues. In some embodiments, the physiological pH ranges from about 7.0 to 7.4. In some embodiments, biodegradable materials are not hydrolytically degradable but can be fully degraded via enzymatic action to fully degrade. In some cases, biodegradable materials are hydrolytically or enzymatically degradable, or combinations thereof. In some embodiments, the polymer or polymer foam is biodegradable, but it does not biodegrade over the time scale in which it is located within a body cavity. In such cases, the polymer foam can remain structurally stable while being inserted into the body cavity, while ensuring that any remnants of the polymer foam that remain within the body cavity after removal can be biodegraded. For example, in some embodiments, the biodegradable polymer foam does not significantly biodegrade within the body cavity prior to removing the foam via surgical intervention.

The polymer or polymer foam may be biocompatible, in some instances. One of ordinary skill in the art can determine biocompatibility based upon the IS0-10993 standard. For example, PGS is known to satisfy the IS0-10993 standard for biocompatibility. In some embodiments, chemical modifications (e.g., attachment of a pendant group, etc.) to the PGS backbone do not alter its biocompatibility. In some embodiments, a polymer that produces known, but acceptable levels of inflammation may be used. Examples of such polymers include poly-alpha-hydroxyacids (e.g., polylactide, polyglycolide, and polycaprolactone) and poly(trimethylene carbonate).

The polymeric foams described herein may be used, in some embodiments, to prevent or limit the movement of a bodily fluid within the body cavity, relative to an amount of movement of bodily fluid that would occur under essentially identical conditions in the absence of the polymer foam. "Essentially identical conditions," in this context, means conditions that are similar or identical other than the presence of the polymer foam. For example, otherwise identical conditions may mean that the body cavity is identical, the conditions within the cavity are identical, but where no polymer foam is located within the body cavity. In some embodiments, the polymer foam may be used to reduce an amount of bleeding within a body cavity. The polymer foams may also be used to prevent or limit the movement of bile or other digestive fluids, interstitial fluid, or any other suitable fluid. In some embodiments, preventing or limiting the movement of bodily fluid comprises immobilizing and/or stabilizing blood clots. Preventing or limiting the movement of a bodily fluid may comprise, in some instances, the movement of bodily fluids into the cells of the polymer foam. Such movement of fluid into the cells may aid in the formation of, for example, blood clots or other stabilizing structures within the foam.

The movement of bodily fluids may be prevented or limited over a relatively long period of time. For example, in some embodiments, the polymer foam can prevent or limit movement of a bodily fluid within the body cavity for at least about 3 hours, at least about 6 hours, at least about 12 hours, at least about 24 hours, at least about 3 days, or at least about 1 week.

In some cases, the movement of bodily fluids may be prevented or limited via the application of pressure. For example, the formation of the polymer foam may involve volumetric expansion of the polymer. In some embodiments, the expansion of the polymer may result in the application of a pressure to a surface within the body cavity.

In some embodiments, the polymer foam may be used to reduce the amount of bleeding within the wound cavity relatively quickly. This may be important, for example, in avoiding hyperfibrinolysis. In some cases, the polymer may be designed to cross-link quickly, for example, by tailoring the polymer to have functional groups that crosslink quickly, by adding catalysts, or by other known means. Suitable catalysts for use in embodiments of the present invention include amine based compounds, preferably tertiary amines, triethylenediamine (TEDA, DABCO, DABCO 33-LV), bis(2-dimethylaminoethyl)ether (Niax Al), trimethylaminoethyl-ethanolamine, 1,2-dimethylimidazole. In addition, the pores of the foam can trap blood and allow it to coagulate in stagnant areas. In addition, the rate at which the amount of bleeding is reduced can be controlled by adjusting the amount of reactive pendant groups.

In addition to gas-forming pendant groups, other active agents may also be included as pendant groups on the polymer. For example, the polymer foam can include groups used to stimulate desirable cellular responses such as fibroplasia, angiogenesis and epithelialization. In some embodiments, the polymer or polymer foam may be covalently bonded to a surface within the body cavity, for example, through a pendant group.

In some embodiments, the polymer or cross-linked product may comprise at least one pendant group (e.g., at least one pendant group) that can bind to tissue or injured tissue (e.g., inflamed tissue, bleeding tissue, a wound site, etc.) within the body cavity. The binding of the pendant groups to the tissue or injured tissue can be covalent or non-covalent. The tissue or injured tissue may comprise one or more molecules that would not be present in or near uninjured tissue as is the case, for example, when subendothelial surfaces are exposed. By including such pendant groups, a polymer or cross-linked product could be made that selectively binds to tissue or injured tissue, in comparison to uninjured tissue. Such binding may limit or prevent the movement of bodily fluid within the body cavity, in some embodiments. Examples of chemicals that may be targeted by pendant groups on the polymer or polymer foam include, for example, von Willebrand Factor, collagen (e.g., collagen I and IV), a fibroblast growth factor, laminin, elastin, localized coagulation factors in their activated form (e.g., fibrin, thrombin, factor Xa, etc.), among others. Example of types of pendant groups that may be bound to the polymer or polymer foam for such uses include, for example, peptides, carbohydrates (e.g., oligosaccharide sequences), aptamers.

One of ordinary skill in the art will be able to identify other compounds in tissue or injured tissues and perform screening tests to determine suitable pendant groups that could be used to bind with those compounds. For example, in vivo screening, for example by phage display technology, of a large library of possible pendant groups (e.g., permutations of peptide sequences fused to a phage surface protein, a collection of carbohydrate molecules, etc.) could be performed (e.g., in rodents) to identify pendant groups that bind specifically to wounded organs. The pendant group could then be identified (e.g., via sequencing for peptides) from each organ. For example, a sequence that appears in all organs or injured organs could be identified. Subsequent testing (e.g., in vivo testing in uninjured animals) could be performed to verify that the pendant group does not bind to tissue in the absence of injury.

In some cases, human protein targets can be used to find pendant groups that bind selectively to the injured site. For example, human fibrin, which is generally present where injuries to blood vessels have occurred, can be used for screening, potentially mitigating the risk present in the in vivo approach where there could be sequence and conformational differences between animal and human targets. Binding levels to fibrin can be assessed using, for example, fluorescently tagged molecules, and compared against, for example, fibrinogen, a precursor of fibrin that is ubiquitous in blood plasma. The pendant groups showing highest selectivity to fibrin over fibrinogen could be selected for use in the polymer composition.

In addition to targeting tissues or injured tissues, pendant groups may be used to stabilize tissue or injured tissue. For example, pendant groups (e.g., $CO_2$-forming groups) may covalently bond to tissue, in some cases, which may lead to the sealing of one or more openings within a body cavity. Such binding can aid in limiting or preventing the movement of bodily fluid within the body cavity, in some cases. In some embodiments, the concentration of isocyanate in the polymer or a cross-linked product can affect the extent to which binding between the polymer and tissue occurs. Specifically, increasing the isocyanate levels can serve to increase and reinforce the polymer-tissue contact area, potentially producing a stronger and longer-lasting seal. Increasing the level of isocyanate in the polymer can also increases the crosslink density, potentially resulting in a more rigid material that may break more easily at the polymer-tissue interface (e.g., when the body is moved). Therefore, the concentration of isocyanate may be selected, in some cases, to balance between these two effects.

In another embodiment, the polymer properties are selected such that minimal covalent binding of the foam to tissue is observed. The foam, however, can be bound to tissue by different non-covalent forces, such as electrostatic, Van der Waals, or capillary. Minimal covalent binding of foam to tissue can facilitate easy foam removal and prevent adhesions, such as abdominal adhesions, during the healing process.

In some cases, non-isocyanate pendant groups may be used to stabilize the polymer-tissue interface. For example, the polymer may comprise aldehyde reactive groups, which can be used, for example to bind tissue proteins. Aldehyde groups may be attached by, for example, attaching ethanolamine to the polymer, followed by oxidizing the pendant hydroxyl group to form an aldehyde group. In some instances, pendant groups that selectively bind to fibrin may be used to stabilize the clot-polymer interface. In addition, pendant groups may be selected that compete with plasminogen and its activators for fibrin binding sites, blocking the activation of fibrynolytic cascade.

In some embodiments, the polymer (or the compounds used to make the polymer) are chosen such that they comprise one or more pendant hydroxyl groups. The hydroxyl groups may serve, for example, as sites at which pendant groups are attached to the polymer. For example, glycerol and sebacic acid both contain hydroxyl groups that may be used to impart functionality to PGS. As a specific example, pendant peptides can be introduced onto polymers using a two-step reaction scheme in which the polymer hydroxyl groups are first activated with carbonyldiimidazole (CDI) and then coupled to the amine-terminus of the peptide, as shown below. This chemistry can result in high coupling efficiencies.

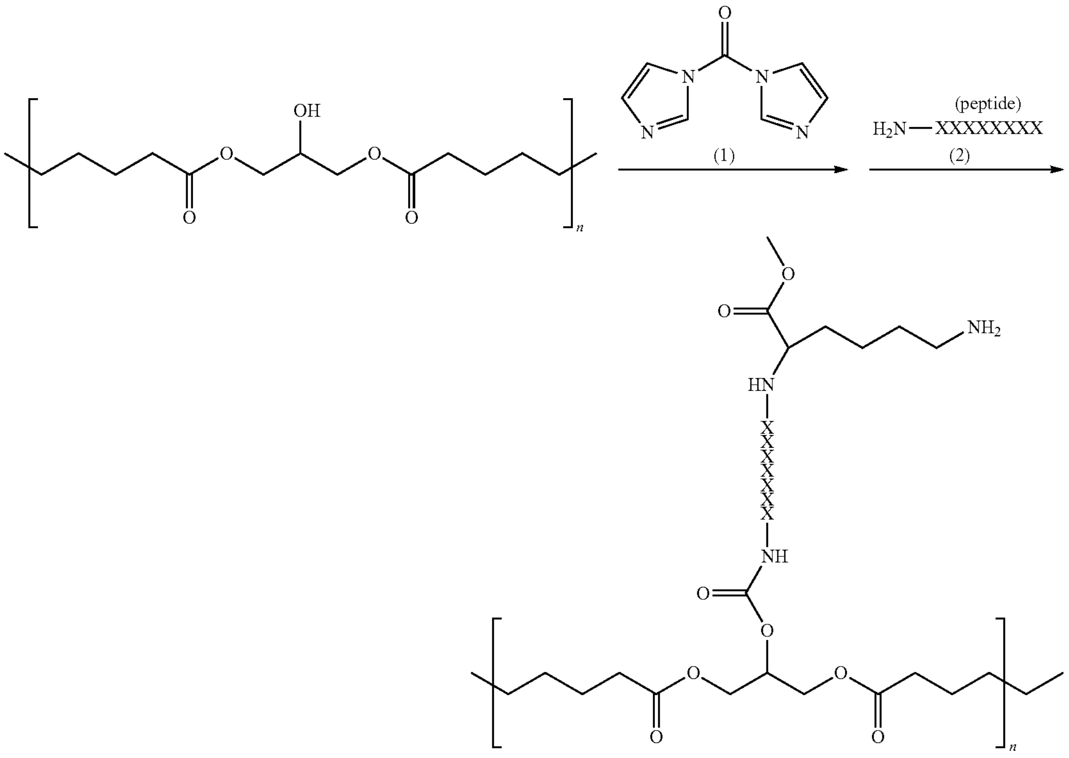

In some instances, a drug may be delivered to the body cavity with the polymer. In some embodiments, the polymer may comprise a drug. For example, a drug (or a plurality of particles containing one or more drugs) may be dispersed within the polymer. Example of such drugs include, but are not limited to, antifibrinolytic compounds (e.g., aminocaproic acid, tranexamic acid, etc.), anti-fibrotic compounds, antimicrobial compounds (e.g., antibiotics), anti-inflammatory compounds, analgesics, pro-coagulant compounds, growth factors, and vasoconstrictors. Drugs that comprise amine groups may, in some cases, be isolated from isocyanates within the polymer, for example, to prevent unwanted reaction during the cross-linking step. Isolation can be achieved by encapsulating drugs into secondary particles and loading them into the polymer at the time of delivery to the body cavity. In addition, encapsulation may be used to release the drugs at a controlled rate. In some embodiments, a drug may be incorporated into a fiber, which may be included in the polymer. The drug release rate from the fiber can be controlled by varying composition and structure (e.g., thickness or other dimension, presence of sheath) of fiber. For example, the fiber can be designed to deliver an initial burst release shortly after the deployment of the polymer, followed by sustained delivery (e.g., over the time period in which the polymer foam will be left in the body cavity).

The polymer may be combined with a second agent (and, optionally, a third agent, fourth agent, etc.), in some cases, before or after the polymer is transported to the body cavity. The second agent may comprise, for example, a compound that accelerates at least one of cross-linking and foaming, relative to a rate of at least one of cross-linking and foaming that would have occurred in the absence of the second agent. For example, in some embodiments, the second agent may comprise an amine (e.g., a polyamine). The amine compound may serve to increase the rate at which the polymer cross-links, which may also reduce the amount of time required to reduce or eliminate the movement of a fluid (e.g., blood) within the body cavity. The second agent may comprise, in some cases, at least one of lysine, spermine, spermidine, hexamethylenediamine, polylysine, polyallylamine, polyethylenimine, and chitosan. In some cases, the second reagent may comprise a carbonate or a bicarbonate which may be used, for example, to produce $CO_2$ gas in situ, as described above. In some embodiments, the second reagent can comprise an acid which may be used, for example, as a reactant in the $CO_2$-producing reaction. The acid functionality may comprise, for example, a carboxylic acid pendant group attached to a polymer chain or blended with a polymer to form a mixture. In some cases, the second reagent can be native in the body (e.g., bicarbonate in the blood). In other cases, the second agent may originate from outside the body cavity. For example, the second agent may be, for example, supplied to the body cavity along with the polymer.

In some embodiments, the combination of the second agent with the polymer produces a polymer foam with significantly different mechanical properties (e.g., elastic modulus, yield strength, breaking strength, etc.) than would have been produced in the absence of the second agent. For example, addition of the second agent may lead to increased cross-linking among polymer molecules, potentially producing a stiffer foam.

The combination of the second agent with the polymer may, in some embodiments, prevent or limit bleeding within the body cavity, relative to an amount of bleeding that would occur under essentially identical conditions in the absence of the second agent. In some embodiments, bleeding may be reduced due to the increased rate of cross-linking or foaming mentioned above. In some cases, the second agent may comprise a pro-coagulant compound (e.g., thrombin, fibrinogen, factor X, factor VII).

The second agent may be stored in a container separate from the polymer, for example, to prevent unwanted reaction between the polymer and the second agent outside the body cavity. In some embodiments, a container can be used that keeps the polymer and the second agent separated while stored or transported, but allow for mixing at the outlet nozzle or within the body cavity when the contents are expelled. The outlet nozzle can mix multiple componets (>2) including gases in a static or dynamic manner. Examples of static mixers are Low Pressure Drop (LPD) mixers, Bayonet mixers and Interfacial Surface Generator (ISG) mixers. Examples of dynamic mixers are impellers, and rotary static mixers. Nozzles will handle low and high pressure differentials during dispensing. The container may also be designed to mix the components immediately prior to dispensing by breaking the barrier between each of the components and allowing them to mix. Mixing can occur manually such as shaking the canister or chambers can be under vacuum and when the barrier is broken a vortex will be created to mix the components.

In another embodiment, additives can be added to the polymer that absorb the heat generated during the cross-linking reaction. For example, materials in the form of micro or nanoparticles, spheres or fibers can absorb the heat by undergoing a phase change (e.g. melting) or glass transition and thereby reduce the heat absorbed by biological tissues. For example, biodegradable fibers made of polycaprolactone can melt at ~60° C., absorbing the generated heat and reducing tissue damage.

In some embodiments, the body cavity can be imaged. The ability to image the body cavity can allow for efficient localization and repair of an injury, stabilization of a wound, etc. In some embodiments, pendant groups on the polymer or polymer foam can be utilized to aid in imaging the body cavity. For example, a contrast agent can be introduced into the blood stream of a subject in which the body cavity is located, and the contrast agent may be capable of selectively binding to pendant groups of the polymer. Examples of contrast agents include, for example, colored, fluorescent, or radio-opaque imaging entities. In some embodiments, the contrast agents emit electromagnetic radiation in the near-infrared range (e.g., about 700 to about 1000 nm) upon interacting with the polymer foam. As a specific example, quantum dots (QD) may be used as contrast agents. In some cases, fluorescent organic tags (e.g. fluoroscein isocyanate) or radio-opaque chelating groups (e.g., Gd3+) can be used with appropriate imaging equipment. In another example, the contrast agents listed above may be attached as pendant groups to the polymer or dispersed in the polymer to aid in visualization.

A variety of mechanisms can be employed to remove polymer or polymer foam from the body cavity or from placement on tissue. In some embodiments, at least part of the polymer foam is removed via surgical intervention. For example, the polymer foam may be cut out of the body cavity, in some instances. In some cases, surgical intervention may be sufficient to remove the bulk of the polymer foam material (e.g., at least about 80%, at least about 90%, etc.) from the body cavity. The polymer or the pendant groups bonded to the polymer may be selected, in some cases, such that the resulting polymer foam can be removed from a body cavity. In some embodiments that employ a biodegradable polymer or polymer foam, the foam or the remainder of the foam after surgical removal may biodegrade over time.

In some embodiments, the foam may be degraded by applying an external stimulus to the foam. Such methods may be useful, for example, when some polymer or polymer foam material remains physically inaccessible after surgical removal due to, for example, deep tissue penetration. Examples of external stimuli that may be applied to degrade the polymer foam include, but are not limited to, UV radiation, heat, or a chemical (e.g., a chemical introduced into the blood stream of a subject in which the body cavity is formed).

Degradation of the polymer foam may be achieved, in some cases, via reversible crosslinks in the polymer or polymer foam. In some cases, the type of cross-link or external stimulus type can be selected such that the polymer foam is selectively and controllably depolymerized. Upon reversion to the uncrosslinked state, the polymer or polymer foam can, in some cases, be removed from the cavity using, for example, saline.

Reversible cross-linking can be accomplished by, for example, modifying a pendant group of the polymer to include bis(2-isocyanatoethyl) disulfide. Such chemistry may be particularly useful, for example, when isocyanate chemistry, which may not be reversible using the external stimulus of choice, is used to foam the polymer. The disulfide group can be readily cleaved with, for example, glutathione. In this example, the sulfur-sulfur bond can be broken through a disulfide exchange reaction, enabling selective cleaving at the disulfide bonds by application of, for example, a glutathione solution. As another example, cinnamic acid groups can be attached to the polymer such that reversing the cross-links can be accomplished by application of UV light.

Figure 4A:
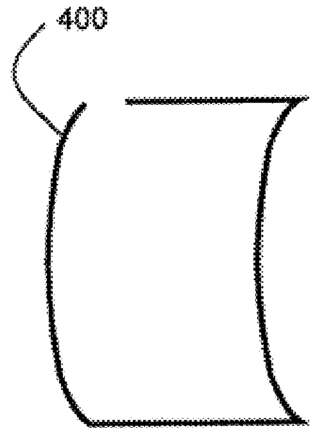
FIGS. 4A-4C include exemplary schematic illustrations of the formation of a polymer foam.
Figure 4B:
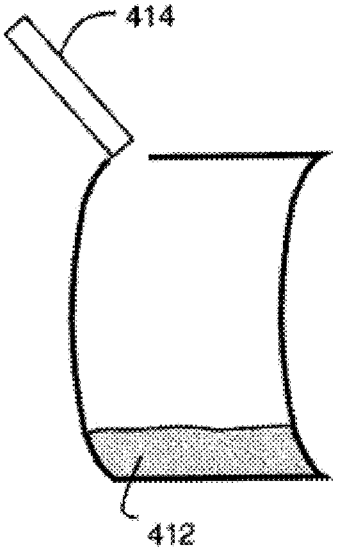
Figure 4C:
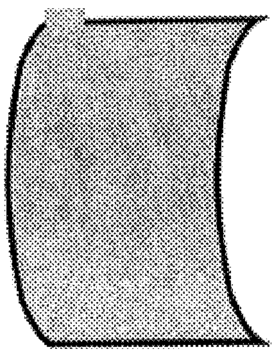

In some embodiments, the polymer foam is not formed within the body cavity, but rather, the foam is formed outside of a body cavity, and is later inserted into the body cavity. For example, FIGS. 4A-4C include schematic illustrations of the formation of a polymer foam within a mold. In FIG. 4A, mold 400 is illustrated. FIG. 4B illustrates the step of supplying polymer 412 to the mold via source 414. FIG. 4C illustrates the expansion of the polymer to form a polymer foam upon supplying a gas to the polymer. The polymer may, in some case, expand to conform to the shape of the mold. The molded polymer then may be inserted into a body cavity. In still further embodiments, the polymer may be formed into a polymer foam outside of a body cavity and without the use of a mold. The polymer foam may then be formed into an appropriate shape by using an appropriate method such as, for example, cutting, grinding, or any other suitable method.

In another aspect of the present invention, polymer foams are used to prevent tissue adhesions. These include, but are not limited to fibrotic scars that form between tissues following an injury or surgical intervention as well as other tissue adhesions known to those of ordinary skill in the medical arts. Examples of regions of the body where adhesions have been described include: the abdomen, pelvis, spine, cardiothoracic space and joints as well as at other locations within the body. These tissue adhesions cause serious clinical consequences. For example, irreversible bowel obstruction in the abdominal cavity, infertility in the pelvic region, chronic pain following back surgery and pain and limited mobility following joint surgery as well as other debilitating disorders known to those skilled in the medical arts.

To prevent tissue adhesions, embodiments of the polymer foam are administered at or near tissue following damage or surgery. By contacting the tissue surfaces with the foam and allowing its expansion, folds and inaccessible surfaces are also covered when direct application is not possible. The polymer's expansion ratio, compliance, hydrophobicity, viscosity and curing time may be optimized for each body region in order to facilitate complete coverage. The volume of polymer foam required may also be varied depending on anatomical location and the area of tissue damage. In some embodiments, the amount of foam administered may be at least 1 ml, at least 10 ml, at least 100 ml, or more. In another embodiment, foam expansion is minimal permitting the volume administered and other delivery factors lead to complete coverage.

All polymer formulations described are contemplated for use in preventing tissue adhesions. A preferred embodiment utilizes PGS as a component of the foam. A more preferred embodiment includes isocyanate-functionalized PGS that cures in the presence of body water. In this embodiment, interchain hydrogen bonding results in an increase in modulus. In another embodiment water may be mixed with the isocyanate-functionalized PGS during administration to facilitate curing. In another embodiment, the isocyanate-functionalized PGS is mixed at the time of administration with a polyamine (e.g. lysine, PEG-amine). This polyamine acts as a curing or crosslinking agent. Variation in the amount of polyamine and/or type of polyamine used enables control of mechanical properties of the cured polymer.

In another embodiment, PGS acts as a polyol and can be mixed with an isocyanate containing compound to form a cross linked foam. In these cases, foam formation is obtained and enhanced by mixing gas into the formulation to create pore nucleation sites, or by adjusting the levels of surfactants that stabilize the foam pores during their formation and expansion. In other embodiments, the polymer does not foam or foams minimally allowing for flow over the tissue surfaces. This allows for curing into a gel coating. In these cases, PGS is cross linked under conditions that minimize foam formation by limiting or preventing gas into the formulation and/or reducing the levels of surfactants resulting pore stabilization. In addition, PGS can be gelled or cross linked by mixing with a component that does not generate a gaseous by-products upon reaction with PGS.

In yet other embodiments two or more different PGS polymers can be combined during administration. These polymers then react and crosslink into a gel or foam. The type and ratio of PGS polymers used impact the foaming, gelling, curing and mechanical properties.

In another embodiment drug-loaded objects are incorporated in the foam or gel at or before administration. Incorporation of drug-loaded objects into a polymer during administration is accomplished by those methods known to those skilled in the medical and pharmaceutical formulation arts. Examples of drug-loaded objects include: microspheres, microfibers, core-sheath microfibers, core-sheath nanofibers, nanoparticles, nanospheres, nanofibers or pure particles of drug. Preferably drug is released from these objects over a period of 7 days. More preferably the drug is released up to 14 days. Drug may be released for up to 30 days or longer. Preferably the kinetic release profile for the drug provides approximately the same dose of drug throughout a given period of time.

In certain embodiments, the invention relates to liquid formulations that are delivered to a body cavity and form foam implants in situ. The liquid formulation or formulations optionally include an entrained gas or a dissolved gas. In preferred embodiments, the resulting foam implant provides hemostasis when applied near one or more sites of hemorrhage. Foam implants of the invention are preferably biocompatible, bioabsorbable, can be removed from the body with standard surgical procedures, and do not induce adhesions.

In certain embodiments, the invention is a polyurethane foam that is formed in situ from a two-part formulation as previously described. The first part of the formulation includes an isocyanate compound such as hexamethylene diisocyanate (HDI), toluene diisocyanate (TDI), methylene diphenyl diisocyanate (MDI) or a mixture of MDI isomers, polymeric MDI, isocyanate-functionalized prepolymer, or a polymeric isocyanate having a functionality of preferably between 2.0 and 3.0. The second part of the formulation includes a hydroxyl-functionalized polymer (polyol). The preferred viscosity of the first and second parts of the formulation is 1 to 3,000 cP, and preferably about 2,400 to about 2,600 cP. The polyol phase optionally has multiple polyol species, catalysts, surfactants, chain extenders, cross linkers, pore openers, fillers, plasticizers and water. Air, carbon dioxide or other auxiliary blowing agents are optionally entrained into either the isocyanate or polyol phases prior to delivery to the patient or, alternatively, are introduced during delivery as a component of the formulation.

The invention will be better understood in the context of certain advantageous characteristics exhibited by foams and formulations of the invention: (i) transport to sites of injury; (ii) lack of interference with bodily functions; (iii) facilitation of hemostasis; and (iv) creation of seals at sites of injury.

Transport to Sites of Injury:

In certain embodiments, foams of the invention reach sites of injury located within tortuous body cavities, around or across anatomical features, through pooled blood, and/or against the flow of blood. In these embodiments, the formulation can be deposited at a site within a body cavity, which site is optionally either proximal to or remote from a site of injury that will be treated; the foam will then travel beyond the site of deposition as foaming and expansion is initiated, for example by moving and expanding along a path of least resistance. The formulation and the foam can be miscible with water, and/or hygroscopic. In certain embodiments, miscibility and hygroscopy are improved by tailoring the pore architecture of the foam to induce capillary action, for example by creating an open-pore architecture within the foam, as is discussed more fully below. In certain preferred embodiments, the mobility of the formulation is facilitated by at least one of the following characteristics: high expansion (10-40× (more preferably 25-35×), or foam density between 1.5-6.3 pounds per cubic foot (pcf)); low viscosity (less than 3,000 cP); foam pore sizes between 10 μm and 10 mm, and hydrophobicity.

Figure 5:
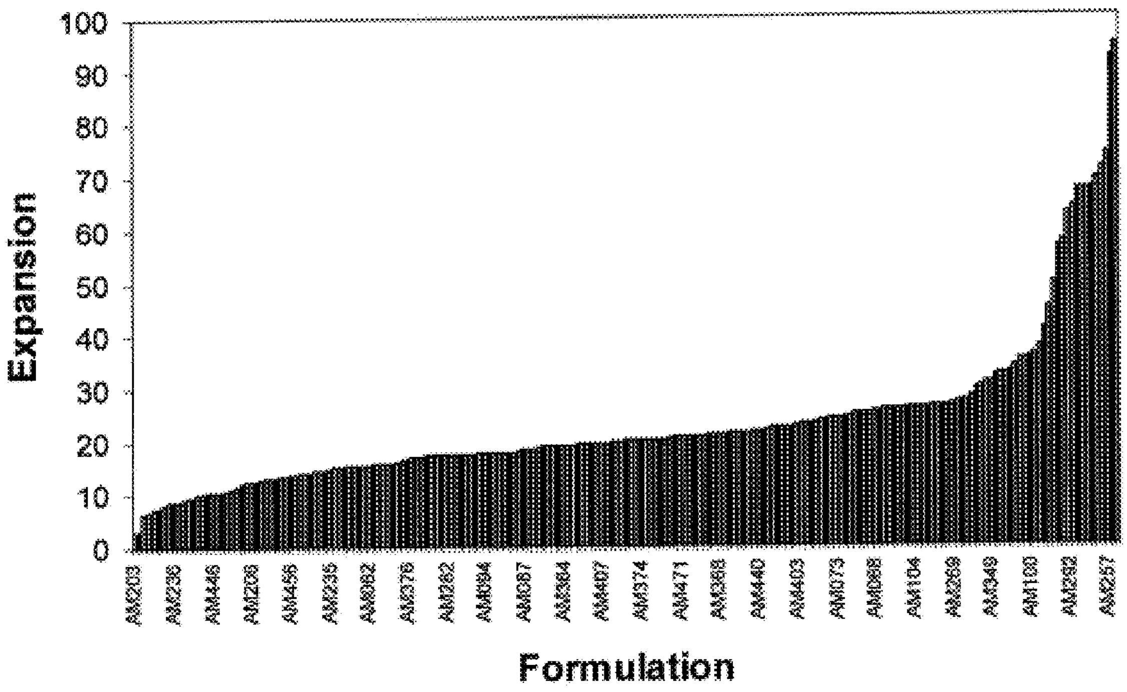
FIG. 5 includes expansion volumes of certain foams of the invention.

With respect to density and expansion, foams have been developed having densities between 10 and 1,000 $kg/m^3$, or having expansions of between 1 and 95 fold, as shown in FIG. 5. In general, increasing the water and/or isocyanate content of the formulation tends to increase the volume expansion. Without wishing to be bound to theory, it is believed that this is due to increased blowing and $CO_2$ evolution. For example, the relatively low 3× expansion of formulation AM203 is increased to 26× in formulation AM201 by increasing the water level of the formulation from 0.45 to 7.2 parts per hundred polyol (pphp). Alternatively, increased expansion can be obtained through the use of blowing catalysts including bis(2-dimethylaminoethyl) ether (DMAEE) and pentamethyldiethylenetriamine (PMDET), or through the use of catalysts that increase both blowing and gelling including triethylenediamine (TEDA), typically up to 10 pphp. For example, the relatively low 12.5× expansion of formulation AM237 is increased to 57.5× in formulation AM244 by increasing the level of TEDA from 0.4 to 3.2 pphp. It may be preferable to increase stabilization of the polymer when the use of catalysts results in increased expansion. Such increased stabilization can be achieved, for example, by adding surfactants such as Tegostab products (B8629, B9736 LF, 4690, 8871, 8523) and Pluronic products (F-68, F-127); adding more gelling catalysts such as heavy metal catalysts such as stannous octoate and zinc octoate; or with other additives such as solid ammonium bicarbonate. For example, formulation AM251 exhibits 95× expansion and is formulated with high water and catalyst levels and a high isocyanate index.

Figure 6:
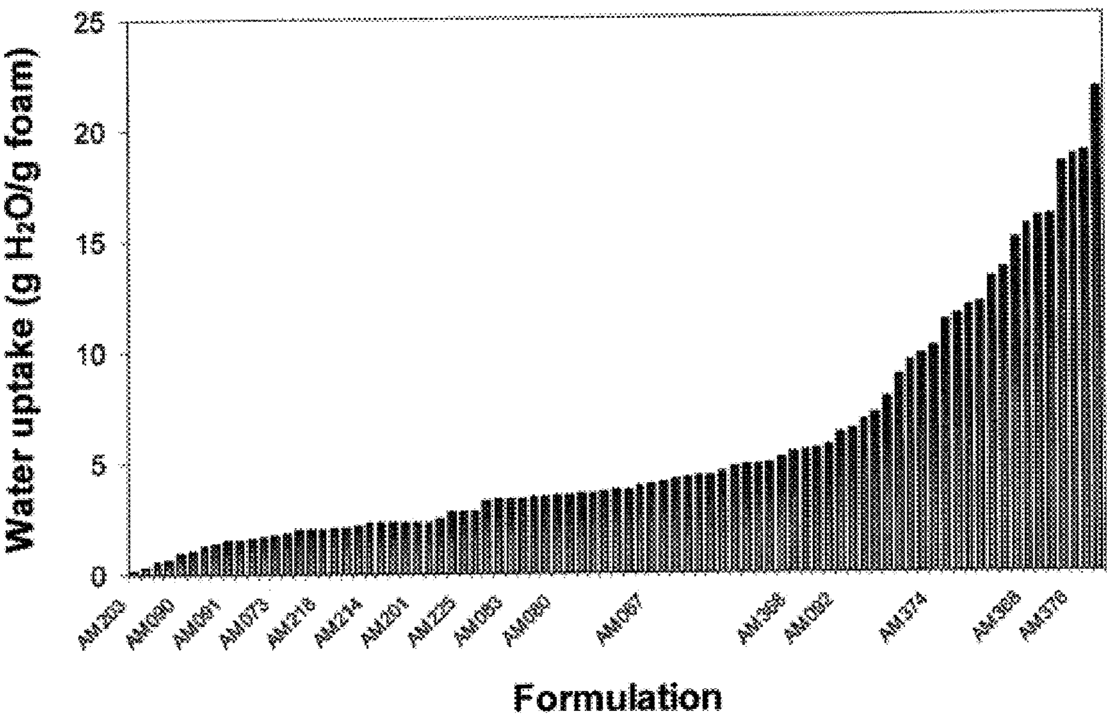
FIG. 6 includes water uptake values of certain foams of the invention.

With respect to hygroscopy and miscibility with water, the water absorption characteristics of foams can be tailored as well. Foams have been developed having both high and low water absorption, as tested by a 4-minute water immersion test. Results of this test for certain formulations of the invention are depicted in FIG. 6. Water absorption of foams of the invention range between 0 and 22 grams of water absorbed per gram of foam. In certain embodiments, high water uptake is achieved by creating a highly open cell or reticulated foam structure. This architecture is formed by balancing the viscosity of the formulation, the rates of blowing and gelling, the catalyst and surfactant types and levels. Additionally, in certain formulations of the invention, the water content is preferably high (5-10 pphp), the isocyanate index is preferably low (10-50 pphp), and a high-functionality isocyanate is preferably used to provide sufficient crosslinking and rigidity at low concentrations to stabilize the foam and prevent collapse. For example, formulation AM373 has a water uptake of 19.8 grams per gram of foam (g/g). The formulation includes a pore opening ingredient (Ortegol 501), a mixture of three polyols for optimal viscosity (Plurcol, trimethylolpropane ethoxylate, and Poly-G) and crosslinking density, and a high-functionality isocyanate (Lupranate M20). Small changes to the level of Ortegol 501, the amount of water (<0.8 pphp), or the isocyanate index (25-35) in the formulation can dramatically decrease the water uptake characteristics of the foam, even though a reticulated foam architecture may still be formed. Compare, for example, formulation AM368, which has water uptake of 6.4 g/g but which retains the reticulated architecture. Thus, it is believed that foam composition affects water uptake apart from its effects on pore morphology or foam architecture. As another example, formulation AM376 exhibits high water uptake and has a reticulated architecture. The formulation includes a hydrophilic polyol, trimethylolpropane ethoxylate 1014 Da (46 pphp) and has high water uptake (19.7 g/g).

In general, the hydrophilicity of the foam may be improved by increasing the amount of polyethylene glycol (PEG)-based polyols used in the formulation relative to hydrophobic polyols such as those based on polypropylene glycol. Water uptake of foams may also be increased as the PEG-based polyol content is increased, though some rebalancing of catalyst, surfactant, isocyanate and other components may be necessary. Small changes to minor ingredients can significantly improve water uptake. For example, by increasing the surfactant level of formulation 122-009-7 by 2.5-fold, water uptake is increased from 6.7 g/g to 21.7 g/g (compare foam 122-009-10).

Figure 7:
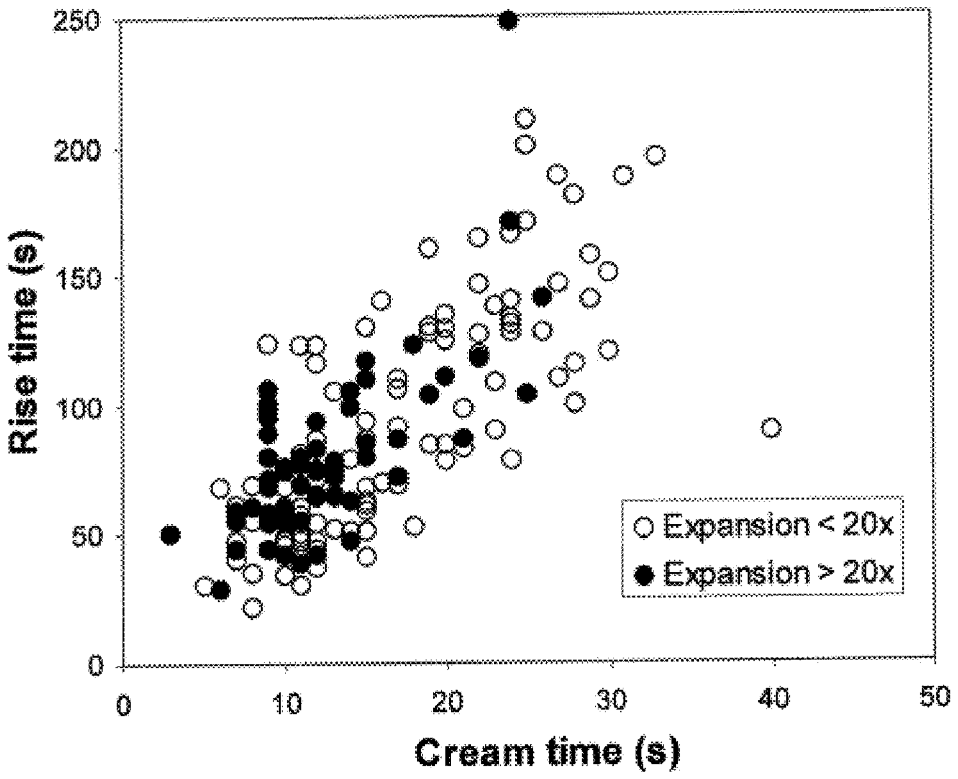
FIG. 7 includes rise time and cream time values for certain formulations of the invention.

Transport to sites of injury may also be improved by providing formulations that can disperse within a body cavity before foaming and/or cross-linking. Delayed foaming and/or cross-linking permits low-viscosity formulations of the invention to penetrate more deeply into tortuous spaces within body cavities. Once the formulation is dispersed, foaming may occur at a moderate rate (on the order of less than 4 minutes) to fully distribute the foam to reach a site or sites of injury. Formulations have been generated that have a variety of reaction kinetics, as measured by cream time, gel time, and rise time and as shown in FIG. 7. Cream time is defined as the time between the start of material mixing and the point at which fine bubbles begin to appear and the foam begins to rise. Gel time is defined as the time at which long "strings" of tacky material can be pulled away from the surface of the foam when the surface is contacted with the edge of a tongue depressor or similar instrument. Rise time is the time at which the foam stops expanding as observed visually.

Foaming kinetics can be altered by adjusting the types and levels of catalysts and inhibitors used in the formulation. In general, the addition of weak acids such as acetic acid or citric acid delays the start of foaming, but has a limited effect on the rate of foaming once it begins. The rate of foaming can be controlled by adjusting the relative levels of blowing and gelling catalysts. For example, the start of foaming is significantly delayed in formulation AM096 (cream time of 25 seconds, rise time of 105 seconds), but the rate of foaming remains similar relative to formulation AM099 (cream time of 9 seconds, rise time of 95 seconds), yet the two differ only in that the level of acetic acid is 0.5 pphp higher in AM096 than in AM099. Generally, preferred embodiments of the invention maximize cream time and minimize rise time to yield cream times of 15 seconds and higher, and rise times of up to 150 seconds.

The viscosity of formulations of the invention can also be controlled and, without wishing to be bound to any theory, it is believed that lower viscosity of the isocyanate and polyol phases improves dispersion within the abdominal cavity. Conventionally, polyols used in polyurethane foam formation are multi-functional, OH-terminated polymers with viscosities of between 250 and 5,000 cP. Because high weight percentages are typically used in the art, polyol phases used in foam formulations tend to have similar viscosities. Formulations of the invention, however, may achieve substantially lower phase viscosities by several means, including (i) using higher quantities of water to dilute high-viscosity polyol components; (ii) using low molecular weight (and hence lower viscosity) polyols; and (iii) using non-reactive diluents to the polyol phase. With respect to diluting high-viscosity polyol components with water, a range of water concentrations of 10-20 pphp may be useful for two-part foaming formulations, while in systems using isocyanate prepolymers water levels of 50-100 pphp are preferred. With respect to using low molecular weight polyols, preferred compounds include propylene glycol, di-tri- and tetrapropylene glycols, ethylene glycol, di- tri- and tetra-ethylene glycols, and low molecular weight, linear or multi-armed, hydroxyl-terminated polymers preferably containing 1-10 repeat units such as polypropylene glycols, polyethylene glycols, polytetrahydrofurans, polytetramethylene glycols, and polydimethylsiloxanes. As for non-reactive diluents, between 10-200 pphp of diluent may be added to the polyol phase, and it has been found that a level as high as 300 pphp can be added to some formulations to yield stable foams (e.g. formulation AM1042; 5.6× expansion). Preferred properties for diluents include low viscosity (<50 cP; more preferably 0.5-10 cP), lack of reactivity towards hydroxyls, isocyanates, and other components in the formulation, and biocompatibility. Preferred diluents include propylene carbonate (PC), diethyl malonate, tetraethylene glycol dimethyl ether (TEGDME), and triacetin.

Using low molecular weight polyols and/or diluents, polyol phases have been engineered with viscosities ranging from 17 cP (AM1045) to 2635 cP (AM735). For example, the hydrophobic polyol phase of formulation AM880 (53 cP) combines a low viscosity polypropylene glycol (1200 Da) and the diluents diethyl malonate (15 pphp) with other ingredients. The more hydrophilic polyol phase of formulation AM759 (50 cP) combines trimethylolpropane ethoxylate (1014 Da) with 70 pphp TEGDME and other ingredients. Even with high levels of diluents, foams with high expansion can still be produced (AM1209; 41 cP; 60 pphp TEGDME; 38× expansion) by increasing the catalyst, water, and isocyanate levels.

Using even higher diluent levels (100-300 pphp) enables further reduction of viscosity (e.g. formulation AM1045; 17 cP; 150 pphp PC; 12.1× expansion). In formulations with high levels of diluents, it is noticed that a heterogenous cell structure with large, irregular cells typically forms at the foam base. The addition of ammonium bicarbonate (0.5-20 pphp) can eliminate this heterogeneity. Using ammonium bicarbonate together with high levels of diluents, foams can be generated with >20× expansion (AM1055; 150 pphp PC; 21.8× expansion). Additionally, added diluents may advantageously act as plasticizers and lead to foams with low compression-force at 50% deflection values (CFD), as discussed below (e.g., AM761; 70 pphp TEGDME; 25.8× expansion, 0.3 kPa CFD).

Figure 8:
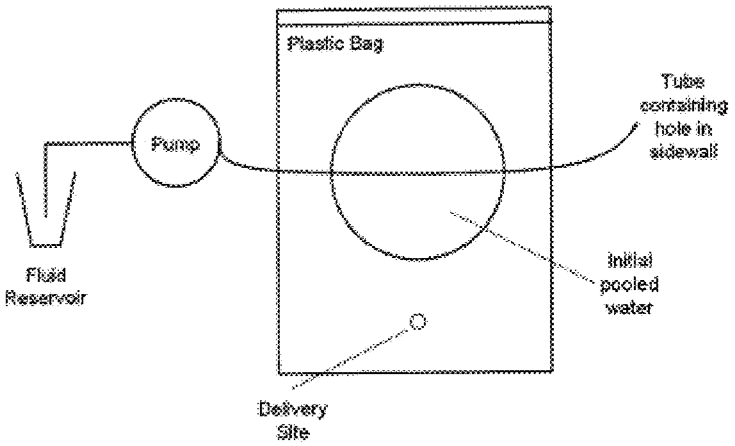
FIG. 8 includes an exemplary schematic illustration of an in situ apposition assay used to evaluate formulations and foams of the invention.
Figure 9:
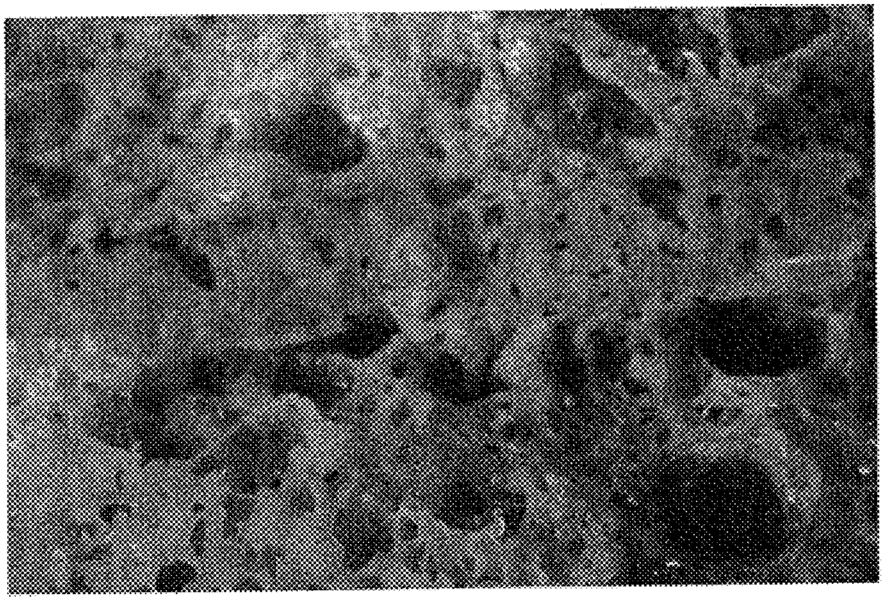
FIG. 9 includes an exemplary photograph of a foam following testing in an in situ apposition assay.

An in vitro test to evaluate dispersion and movement of formulations of the invention has been developed, and is shown schematically in FIG. 8. In the test, a tube is placed within a closed container, a plastic bag. A pump is connected to the tube, and a small hole placed in the tube to create a fluid flow orifice. The tube is submerged within a pool of water of known volume. A formulation is tested by delivering it to the plastic bag using a delivery system and, after a selected period elapses, examining the behavior of the formulation by evaluating, among other things, the apposition to the small hole in the tube, the volume of expansion, and the amount of water absorbed during the blowing, gelling, and curing process. A range of formulations have been examined in this in vitro transport test, and a range of outcomes have been observed. Some formulations have advanced and made conformal contact with the flow orifice (e.g. AM096, AM593). In these formulations, the material around the fluid flow did not contain any gaps, tunnels, or flow pathways that indicated poor transport. For example, formulation AM005 was successful in the transport test; the material contacted the flow orifice and was well apposed. The apposition was close enough to create a dimple in the material from the flow orifice, as shown in FIG. 9. Other formulations have not advanced to the flow tube, or have not made conformal contact with the flow orifice (e.g. AM289, AM374, AM244, AM735). Finally, certain formulations displayed an intermediate result, where the flow orifice is partially covered or has a tunnel path of fluid escape through the material (e.g. AMI 13, AM315, AM746).

A range of formulations have been successful or partially successful in this transport test. Low viscosity, delayed reaction kinetics, and high expansion are all correlated with success in the test. The majority of formulations that have been successful in the test (conformal or near-conformal contact with the flow orifice) have had a viscosity of less than 1200 cP, cream time of more than 10 seconds, and expansion greater than 12×. Finally, hydrophobic formulations have generally performed better in the test than hydrophilic formulations.

Figure 10:
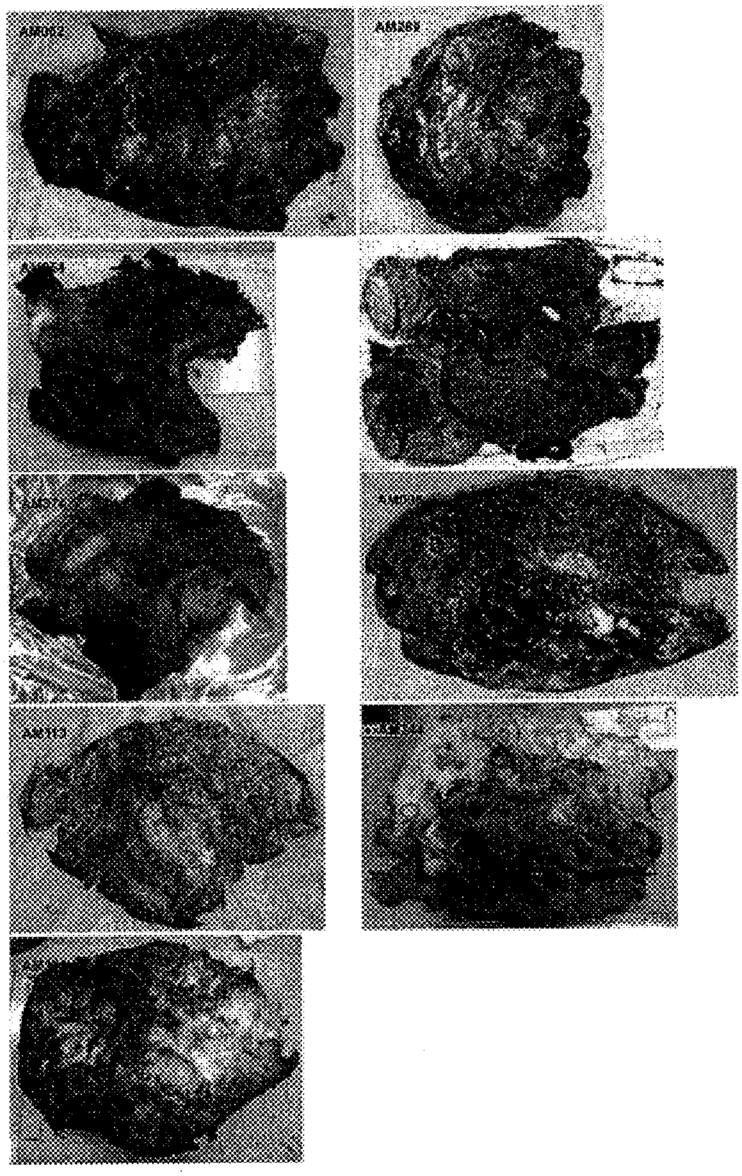
FIG. 10 includes exemplary photographs of foams of the invention following testing in an vivo apposition assay.

An in vivo test of formulations of the invention has also been developed, utilizing a porcine model of grade V splenic hemorrhage in which formulations are deployed in a closed abdominal cavity. FIG. 10 shows foams of the invention deployed in vivo. A semi-quantitative scoring system has been developed for the assay to evaluate transport of the formulations and is outlined in Table 1. Table 2 summarizes the performance of certain formulations in the in vivo transport assay and includes a "Net apposition score" for each. Based on their performance in the assay, formulations were clustered into two groups of high and low scores. Foams with net apposition scores greater than 10 were all hydrophobic (less than 30 pphp PEG), had medium-to-high expansion ratios (13-33×), low-to-medium water uptake levels (12-46%), and with the exception of one formulation, had slow cream times (10-57 seconds). Characteristics of high-scoring formulations are presented in Table 3. By contrast, low-scoring formulations—those with net apposition scores less than 6—were hydrophilic (more than 70 pphp PEG), had low expansion (8-16×), and high water uptake levels (80-95%), as shown in Table 4.

Lack of Interference with Bodily Functions:

Foams of the invention are preferably soft and easily compressed so that they do not interfere with physiological functions such as respiration or cardiac output. For example, in preferred embodiments the foams are sufficiently soft so that, when deployed abdominally to form an implant, they do not interfere with venous blood return through the inferior vena cava. In preferred embodiments, the foams are characterized by CFD values less than 25 kPa and require less than 60 mJ to be compressed 65%. Foams having CFD values greater than 25 kPA but less than 60 kPA may be useful in the invention as well.

The foams preferably apply less than 20 mmHg of pressure during long-term use, though the foams may transiently apply pressures in excess of 20 mmHg during the generation and subsequent dissolution of C02 gas from the isocyanate-water reaction without negative long-term consequences on bodily functions.

Figure 11:
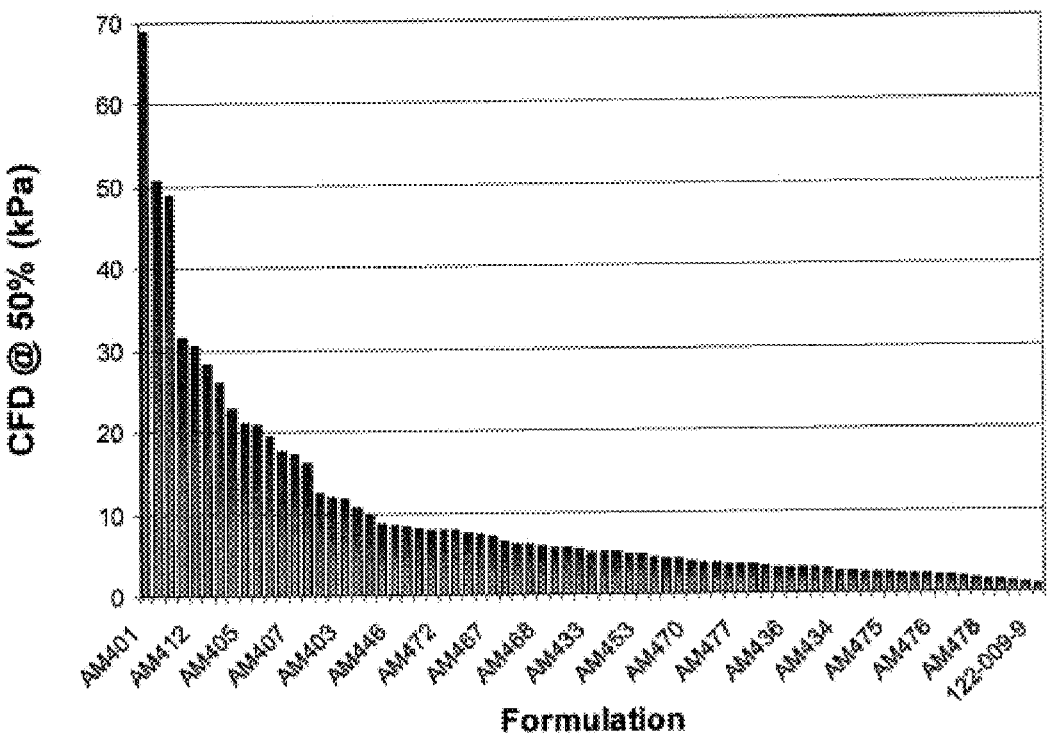
FIG. 11 includes compression force values at 50% compression for certain foams of the invention.

Foams have been developed having CFD values between 0.3 and 100 kPa, as shown in FIG. 11. Soft foams, having low CFD, can be produced using several strategies: (i) using low functionality isocyanates (close to 2.0) so that the crosslink density is minimized, (ii) under-indexing the isocyanate (10-80) so that there is a large excess of polyol and minimal crosslinking, (iii) increasing the polyol molecular weight so that the molecular weight between crosslinks is maximized, (iv) using several polyols to break symmetry and molecular stacking, (v) changing the polyol type to mimimize hydrogen bonding and other intramolecular interactions, (vi) increase expansion as outlined above, and (vii) adding plasticizers. An example of a low CFD foam that has been developed is AM376, which takes advantage of drastic isocyanate under-indexing (25) to achieve 0.8 kPa. AM474 is another low CFD foam of interest (2.3 kPa), which is made by moderate under-indexing (70) of a low functionality isocyanate (Mondur MRS-2), in combination with four polyols to break symmetry. In addition, AM761 is an example of a low CFD foam (0.3 kPa) made by under-indexing the isocyanate (31) and adding diluent to plasticize the matrix (70 pphp TEGDME). Without wishing to be bound to any theory, it is believed that modification of the catalyst, surfactant, water, and additive levels can also lead to significant reductions in the CFD. For example, the CFD of 122-001-10 (4.7 kPa) can be reduced over three-fold by changing the surfactant type and levels to produce AM479 (1.3 kPa).

Figure 12A:
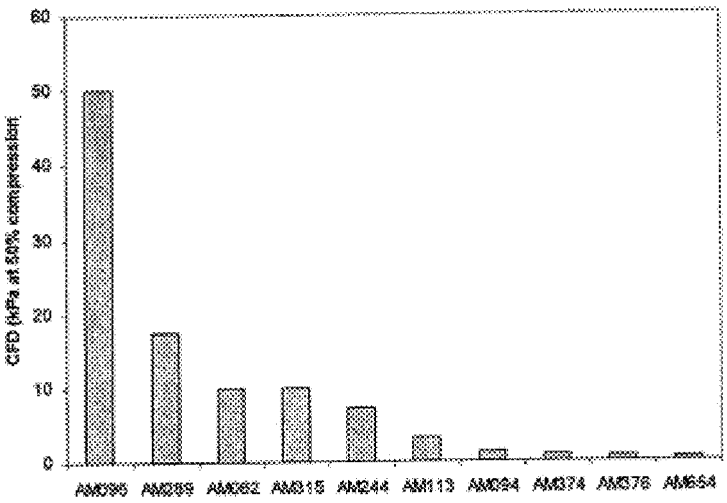
FIG. 12A-C includes compression force values at 50% compression, intra-abdominal pressures, and peak airway pressures for certain foams of the invention evaluated in the in vivo apposition assay.
Figure 12B:
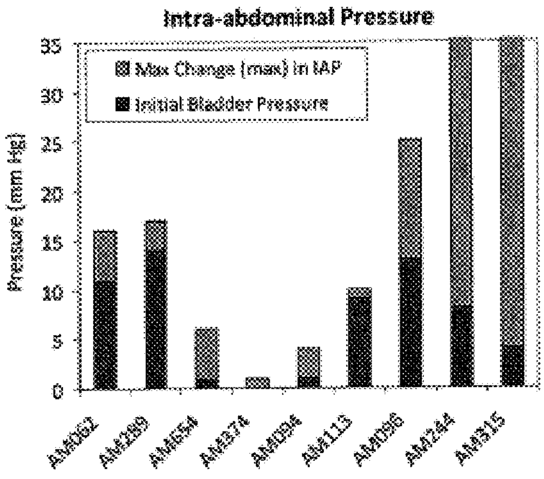
Figure 12C:
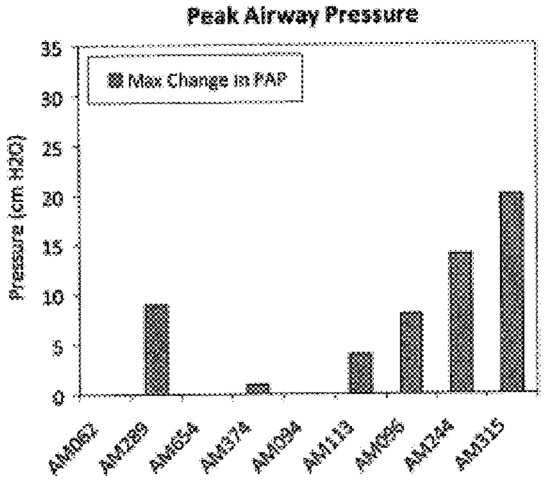

Foams having a range of CFD values, as set forth in FIG. 12*a*, have been tested in vivo and intra-abdominal pressure and peak ventilation airway pressure have been measured to assess interference with bodily functions, as shown in FIGS. 12*b-c*. Three foams tested transiently exceeded an intra-abdominal pressure of 20 mm Hg and two foams exceeded a peak airway pressure of more than 10 cm H20 from baseline. Those foams had intermediate CFD (5-7.5 kPa), but higher expansion ratios (24-33×). Lower CFD materials, such as AM374, AM094, and AMI 13, did not result in a significant increase in pressure.

During the in vivo testing, no effects on cardiac function were observed to be caused or exacerbated by the experimental injury alone.

Facilitation of Hemostasis:

Foams of the invention promote hemostasis when brought into contact with sites of bleeding. In preferred embodiments, foams of the invention have cell and pore structures with characteristics (including size, morphology, and tortuosity) that permit blood to enter the foam but which provide resistance to blood flow. In general, small wounds tend to clot and achieve homeostasis quickly and reliably, while larger wounds do not. High flows from larger wounds are thought to inhibit clotting by disrupting nascent clots and diluting activated clotting factors below effective concentrations and, in larger wounds, clots must reach larger sizes. Without wishing to be bound to theory, foams of the invention may induce hemostasis by changing the "large wound dynamic" to one of many smaller wounds which can clot normally, thus inducing hemostasis. Without wishing to be bound to theory, hemostasis is thought to be induced by foams of the invention through several mechanisms. First, by reducing blood flow, the foams may assist coagulation and allow stable clots to form. In addition to flow resistance, the foams may provide high polymeric surface area for surface fouling, platelet and cell attachment and activation, and initiation of the coagulation cascade. The preferred properties of the foam to facilitate hemostasis include an open cell structure with pore sizes of 0.01-1 mm, high expansion (greater than IOx, or foam density less than 6.2 pct), and a high surface-to-volume ratio. Finally, an additional benefit of providing a foam which allows some blood flow into the structure is a reduction of pressure and the exertion of less force on any seal which may be created between the foam and the site of injury as compared to a foam which does not allow some flow.

Figure 13:
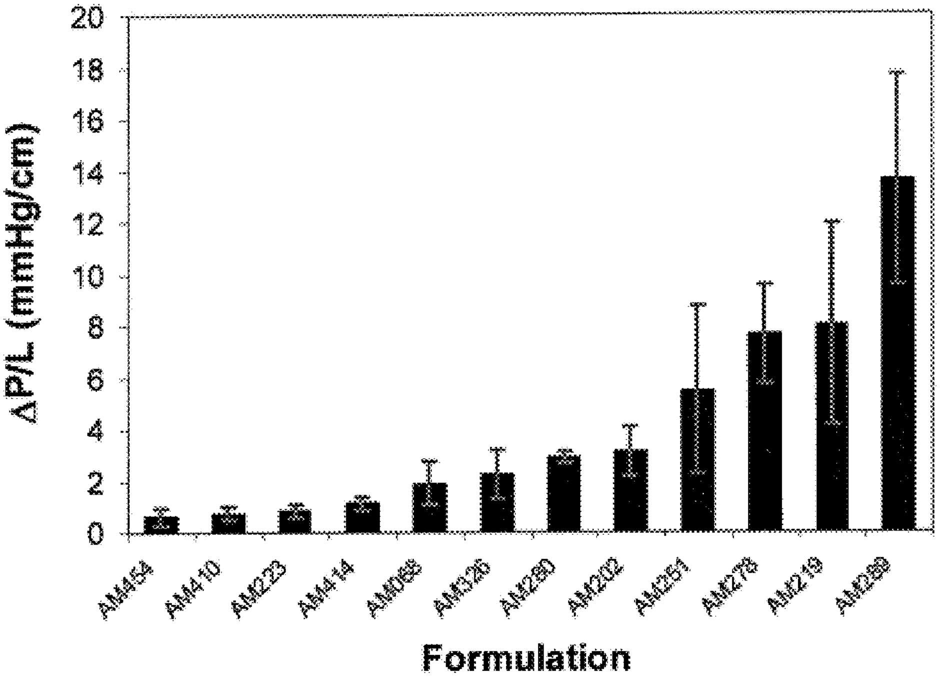
FIG. 13 includes fluid resistivity measurements for certain foams of the invention.
Figure 14:
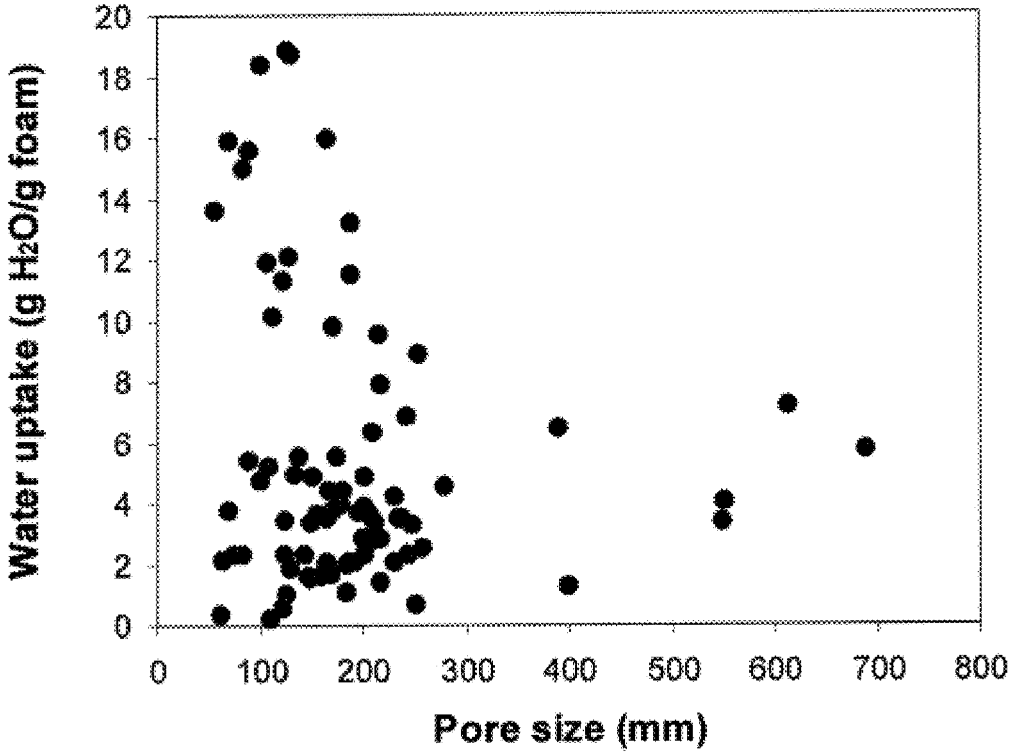
FIG. 14 includes fluid uptake and pore size values for certain foams of the invention.

Foams have been developed with high flow resistance, as determined by measuring the pressure drop needed across a length of foam (P/L) to maintain a certain volumetric flow rate, as shown in FIG. 13. While many foam properties can contribute to hydraulic resistance, the combination of pore size and pore density in particular have been shown to affect resistance. For example, formulations AM219 (t1P/L=8.0 mmHg/cm) and AM289 (i1P/L=13.6 Hg/cm) exhibit high flow resistance but have low pore density (11-13 pores/$mm^2$) and small pore size (avg<130 μm). In contrast, formulations AM374 (t1P/L=1.0 mmHg/cm) and AM376 (t1P/L=1.1 mmHg/cm) have low flow resistance but have high pore densities (>20 pores/mm2) and large pore sizes (avg>240 μm). However, small pore size and low pore density, alone or in combination, are not necessarily sufficient to achieve high flow resistance. For example, the formulation AM474 has low pore density (8 pores/mm2) but a large pore size (avg 225 μm) and has low flow resistance (t1P/L=1.5 mmHg/cm). Similarly, formulation AM368 has a small pore size (avg 130 μm) but a relatively high pore density (19 pores/mm2) and low flow resistance (t1P/L=1.7 mmHg/cm).

Pore density (defined as the number of open pores per unit area) can be controlled by adjusting the types and levels of ingredients in the formulation. In general, pore density can be altered by balancing the isocyanate index, surfactant levels, catalyst levels controlling both blowing and gelling rates, and the polyol viscosity. In many cases, subtle changes to a single ingredient level can drastically change the pore density. For example, it has been found that decreasing the isocyanate index from 45 (in formulation 126-52-4, which has 7 pores/mm2) to 35 (in formulation AM368 which has 19 pores/mm2) while leaving other component concentrations essentially unchanged results in a significantly higher pore density and openness to the structure. In a similar fashion, the pore density of formulation 126-52-2 (12 pores/mm2) can be increased to 19 pores/mm2 (AM368) by only adding 0.37 pphp of the pore opening agent Ortegol 501 to formulation.

Similar to pore density, pore size is affected by a number of ingredient types and levels. For example, the pore size of formulation AM375 (average pore size of approximately 120 μm) can be increased almost three-fold (in AM376; average pore size of approximately 350 μm) by adjusting the relative ratio of Pluracol 816 to TMPEO (17.5:1 to 1:1) while leaving other concentrations essentially unchanged.

The effect of the hydrophilicity or hydrophobicity of foams on the facilitation of hemostasis has also been examined, and is discussed below. The hydrophilicity or hydrophobicity of foams is controlled as discussed above.

Figure 15:
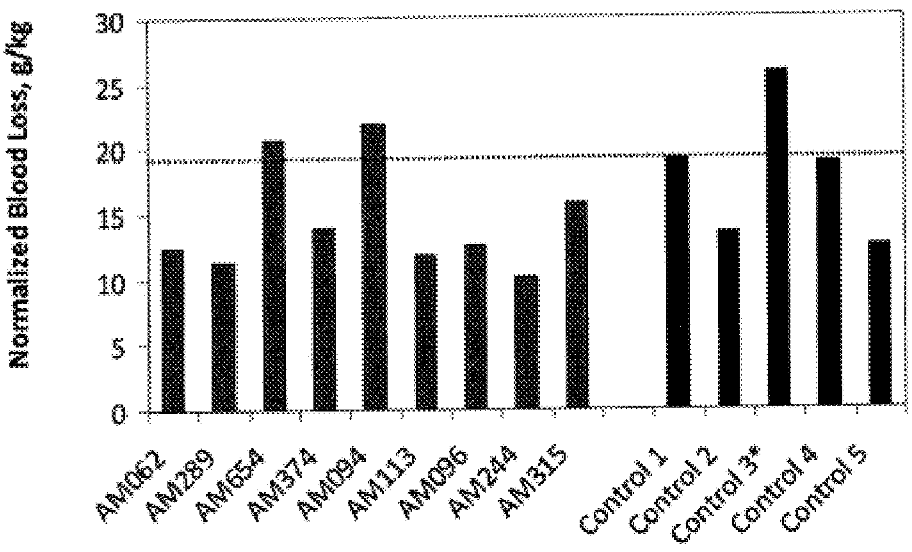
FIG. 15 includes blood loss measurements for certain foams of the invention evaluated in the in vivo apposition assay.
Figure 16:
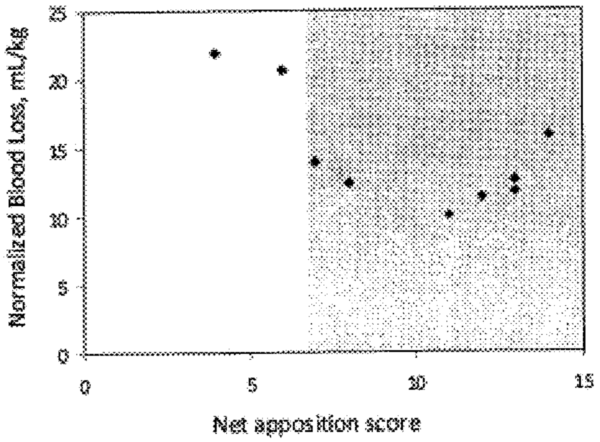
FIG. 16 includes blood loss measurements plotted against net apposition scores for certain foams of the invention evaluated in the in vivo apposition assay.
Figure 17:
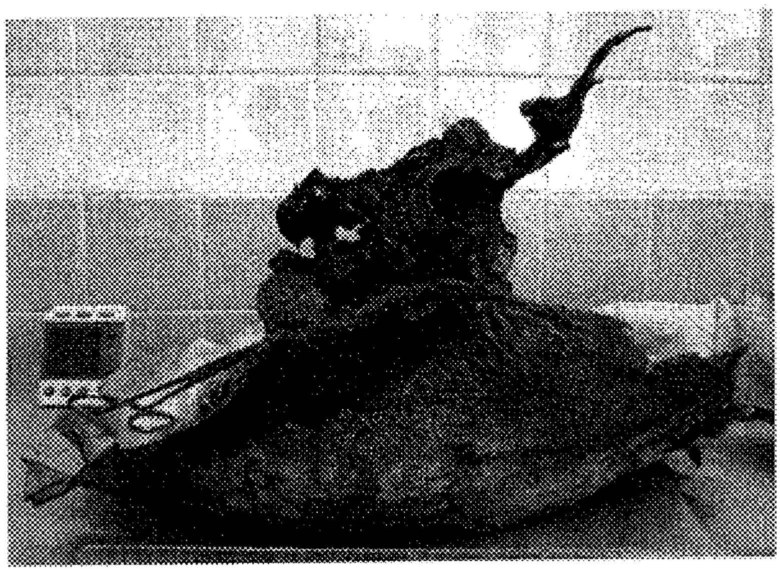
FIG. 17 includes a photograph of a foam of the invention evaluated in the in vivo apposition assay having a projection.
Figure 18:
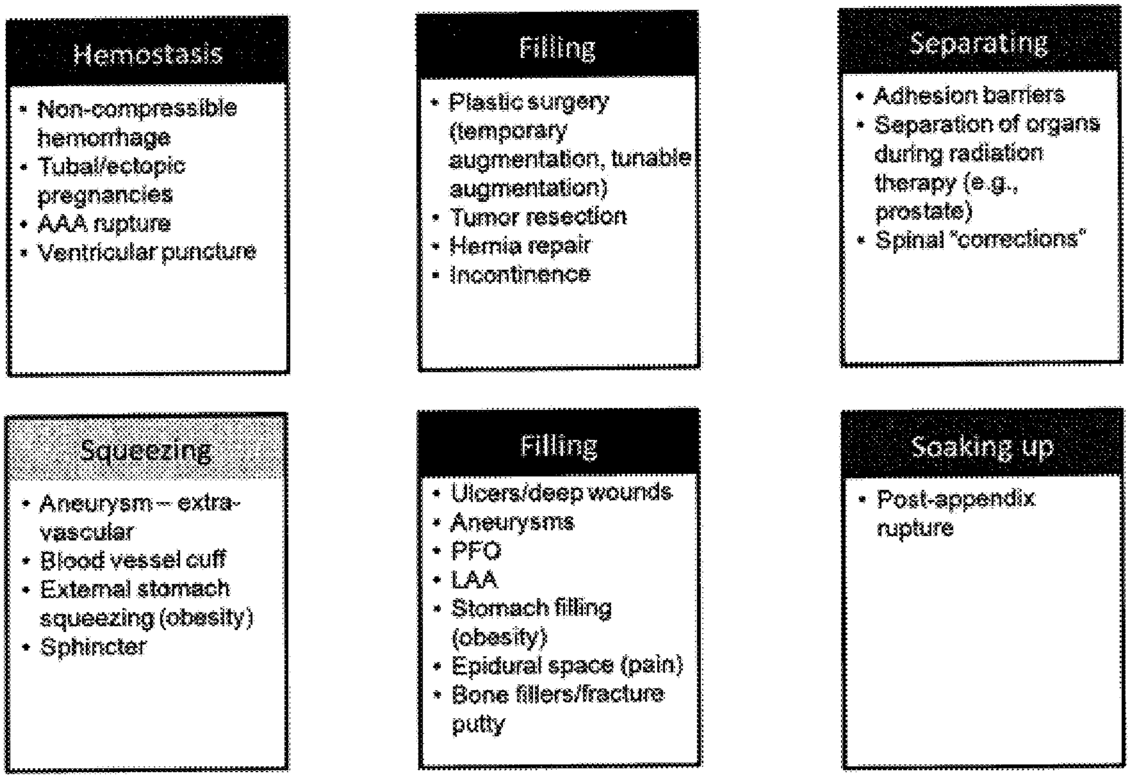
FIG. 18 includes potential indications for foams of the invention according to various foam functionalities.

Hemostasis has been evaluated in as presented in FIG. 15. Values in FIG. 15 are presented in grams of blood lost per kilogram body weight. Of nine foams tested, seven had blood loss values lower than the average of the controls (17.9±5.3 g/kg). Based on the distribution blood loss values, the foams were grouped into those with low normalized blood loss (less than the mean blood loss of the controls) and those with high normalized blood loss (greater than the mean blood loss of the controls). Characteristics of materials in the "low" and "high" blood loss categories are presented in Tables 5-6. Without wishing to be bound to theory, it was noted that there is some overlap in the compositions of foams exhibiting high "net apposition" in the in vivo assay as shown in Table 2, and foams exhibiting low blood loss as shown on Table 5 [and FIG. 13], and there is also some overlap in the composition of foams exhibiting low "net apposition" and high blood loss, as shown in Table 6. For example, formulations AM654 and AM095 both fall in the "high blood loss" and "low net apposition" categories, and both are hydrophilic with low to medium expansion in vivo and high water uptake levels. By contrast, formulations having "low blood loss" and "high net apposition" scores tended to be hydrophobic, have high expansion, slow cream times and low water uptake. No correlations were observed between the degree of blood loss and pore morphology.

Creation of Seals at Sites of Injury:

Foams of the invention may also create a seal when they reach a site of injury, as discussed above. In certain embodiments, sealing is accomplished by non-specific and non-selective binding of isocyanates in the formulation with exposed tissue surfaces. In other embodiments, sealing can be targeted to certain sites of interest such as exposed basement membranes through targeting means.

In some embodiments, a kit including one or more of the compositions previously discussed (e.g., a kit including a polymer that can be foamed in situ, a kit including a polymer foam, a device comprising a polymer or polymer foam and any other additive (e.g., external gas, second agent, etc.), a kit comprising a polymer or polymer foam and a delivery system) that can be used to create and/or deploy a polymer foam, or the like, is described. A "kit," as used herein, typically defines a package or an assembly including one or more of the compositions of the invention, and/or other compositions associated with the invention, for example, as previously described. Each of the compositions of the kit may be provided in liquid form (e.g., in solution, as a liquid-phase polymer, etc.), or in solid form (e.g., a reversibly cross-linked polymer). In certain cases, some of the compositions may be constitutable or otherwise processable, for example, by the addition of a suitable solvent, other species, or source of energy (e.g., UV radiation), which may or may not be provided with the kit. Examples of other compositions or components associated with the invention include, but are not limited to, solvents, surfactants, diluents, salts, buffers, emulsifiers, chelating agents, fillers, antioxidants, binding agents, bulking agents, preservatives, drying agents, antimicrobials, needles, syringes, packaging materials, tubes, bottles, flasks, beakers, dishes, frits, filters, rings, clamps, wraps, patches, containers, tapes, adhesives, and the like, for example, for using, administering, modifying, assembling, storing, packaging, preparing, mixing, diluting, and/or preserving the compositions components for a particular use, for example, to a sample and/or a subject.

A kit of the invention may, in certain cases, include different compositions that can be mixed to form a product. In certain embodiments, the kit may include physically separated chambers to hold the compositions, and a mechanism that is activated by a user or a machine for discharging the compositions and/or mixing them together. As a non-limiting example, the kit may include a dual barrel syringe having first and second chambers that contain first and second compositions, wherein the first and second chambers are physically separated, for example by a wall. In this example, the user may depress the plunger of the dual-barrel syringe to eject the first and second compositions from the first and second chambers. In certain embodiments, the kit also includes a static mixing nozzle, a dynamic mixing nozzle, an impeller, or a mixing chamber to permit the components to mix prior to or during discharge.

A kit of the invention may, in some cases, include instructions in any form that are provided in connection with the compositions of the invention in such a manner that one of ordinary skill in the art would recognize that the instructions are to be associated with the compositions of the invention. For instance, the instructions may include instructions for the use, modification, mixing, diluting, preserving, administering, assembly, storage, packaging, and/or preparation of the compositions and/or other compositions associated with the kit. In some cases, the instructions may also include instructions for the delivery and/or administration of the compositions, for example, for a particular use, e.g., to a sample and/or a subject, or to deliver the compositions of the invention into contact with bodily tissues to prevent, limit, or otherwise control bleeding or the flow of other bodily fluids. The instructions may be provided in any form recognizable by one of ordinary skill in the art as a suitable vehicle for containing such instructions, for example, written or published, verbal, audible (e.g., telephonic), digital, optical, visual (e.g., videotape, DVD, etc.) or electronic communications (including Internet or web-based communications), provided in any manner.

In the compositions of the invention, the term "alkyl" refers to saturated aliphatic groups, including straight-chain alkyl groups, branched-chain alkyl groups, cycloalkyl (alicyclic) groups, alkyl substituted cycloalkyl groups, and cycloalkyl substituted alkyl groups. In some embodiments, a straight chain or branched chain alkyl may have 30 or fewer carbon atoms in its backbone, and, in some cases, 20 or fewer. In some embodiments, a straight chain or branched chain alkyl may have 12 or fewer carbon atoms in its backbone (e.g., $C_1$-$C_{12}$ for straight chain, $C_3$-$C_{12}$ for branched chain), 6 or fewer, or 4 or fewer. Likewise, cycloalkyls may have from 3-10 carbon atoms in their ring structure, or 5, 6 or 7 carbons in the ring structure. Examples of alkyl groups include, but are not limited to, methyl, ethyl, propyl, isopropyl, cyclopropyl, butyl, isobutyl, tert-butyl, cyclobutyl, hexyl, cyclochexyl, and the like.

The term "heteroalkyl" refers to an alkyl group as described herein in which one or more carbon atoms is replaced by a heteroatom. Suitable heteroatoms include oxygen, sulfur, nitrogen, phosphorus, and the like. Examples of heteroalkyl groups include, but are not limited to, alkoxy, amino, thioester, and the like.

The terms "alkenyl" and "alkynyl" refer to unsaturated aliphatic groups analogous in length and possible substitution to the alkyls described above, but that contain at least one double or triple bond respectively.

The terms "heteroalkenyl" and "heteroalkynyl" refer to unsaturated aliphatic groups analogous in length and possible substitution to the heteroalkyls described above, but that contain at least one double or triple bond respectively.

As used herein, the term "halogen" or "halide" designates —F, —Cl, —Br, or —I.

The terms "carboxyl group," "carbonyl group," and "acyl group" are recognized in the art and can include such moieties as can be represented by the general formula:

wherein W is H, OH, O-alkyl, O-alkenyl, or a salt thereof. Where W is O-alkyl, the formula represents an "ester." Where W is OH, the formula represents a "carboxylic acid." The term "carboxylate" refers to an anionic carboxyl group. In general, where the oxygen atom of the above formula is replaced by sulfur, the formula represents a "thiolcarbonyl" group. Where W is a S-alkyl, the formula represents a "thiolester." Where W is SH, the formula represents a "thiolcarboxylic acid." On the other hand, where W is alkyl, the above formula represents a "ketone" group. Where W is hydrogen, the above formula represents an "aldehyde" group.

The term "aryl" refers to aromatic carbocyclic groups, optionally substituted, having a single ring (e.g., phenyl), multiple rings (e.g., biphenyl), or multiple fused rings in which at least one is aromatic (e.g., 1,2,3,4-tetrahydronaphthyl, naphthyl, anthryl, or phenanthryl). That is, at least one ring may have a conjugated pi electron system, while other, adjoining rings can be cycloalkyls, cycloalkenyls, cycloalkynyls, aryls and/or heterocyclyls. The aryl group may be optionally substituted, as described herein. "Carbocyclic aryl groups" refer to aryl groups wherein the ring atoms on the aromatic ring are carbon atoms. Carbocyclic aryl groups include monocyclic carbocyclic aryl groups and polycyclic or fused compounds (e.g., two or more adjacent ring atoms are common to two adjoining rings) such as naphthyl groups. In some cases, the:

The term "alkoxy" refers to the group, —O-alkyl.

The term "aryloxy" refers to the group, —O-aryl.

The term "acyloxy" refers to the group, —O-acyl.

The term "aralkyl" or "arylalkyl", as used herein, refers to an alkyl group substituted with an aryl group.

The terms "heteroaryl" refers to aryl groups comprising at least one heteroatom as a ring atom.

The term "heterocycle" refers to refer to cyclic groups containing at least one heteroatom as a ring atom, in some cases, 1 to 3 heteroatoms as ring atoms, with the remainder of the ring atoms being carbon atoms. Suitable heteroatoms include oxygen, sulfur, nitrogen, phosphorus, and the like. In some cases, the heterocycle may be 3- to 10-membered ring structures or 3- to 7-membered rings, whose ring structures include one to four heteroatoms. The term "heterocycle" may include heteroaryl groups, saturated heterocycles (e.g., cycloheteroalkyl) groups, or combinations thereof. The heterocycle may be a saturated molecule, or may comprise one or more double bonds. In some case, the heterocycle is a nitrogen heterocycle, wherein at least one ring comprises at least one nitrogen ring atom. The heterocycles may be fused to other rings to form a polycylic heterocycle. The heterocycle may also be fused to a spirocyclic group. In some cases, the heterocycle may be attached to a compound via a nitrogen or a carbon atom in the ring.

Heterocycles include, for example, thiophene, benzothiophene, thianthrene, furan, tetrahydrofuran, pyran, isobenzofuran, chromene, xanthene, phenoxathiin, pyrrole, dihydropyrrole, pyrrolidine, imidazole, pyrazole, pyrazine, isothiazole, isoxazole, pyridine, pyrazine, pyrimidine, pyridazine, indolizine, isoindole, indole, indazole, purine, quinolizine, isoquinoline, quinoline, phthalazine, naphthyridine, quinoxaline, quinazoline, cinnoline, pteridine, carbazole, carboline, triazole, tetrazole, oxazole, isoxazole, thiazole, isothiazole, phenanthridine, acridine, pyrimidine, phenanthroline, phenazine, phenarsazine, phenothiazine, furazan, phenoxazine, pyrrolidine, oxolane, thiolane, oxazole, oxazine, piperidine, homopiperidine (hexamnethyleneimine), piperazine (e.g., N-methyl piperazine), morpholine, lactones, lactams such as azetidinones and pyrrolidinones, sultams, sultones, other saturated and/or unsaturated derivatives thereof, and the like. The heterocyclic ring can be optionally substituted at one or more positions with such substituents as described herein. In some cases, the heterocycle may be bonded to a compound via a heteroatom ring atom (e.g., nitrogen). In some cases, the heterocycle may be bonded to a compound via a carbon ring atom. In some cases, the heterocycle is pyridine, imidazole, pyrazine, pyrimidine, pyridazine, acridine, acridin-9-amine, bipyridine, naphthyridine, quinoline, benzoquinoline, benzoisoquinoline, phenanthridine-1,9-diamine, or the like.

The terms "amine" and "amino" are art-recognized and refer to both unsubstituted and substituted amines, e.g., a moiety that can be represented by the 30 general formula: N(R')(R")(R'") wherein R', R", and R'" each independently represent a group permitted by the rules of valence. An example of a substituted amine is benzylamine.

Any of the above groups may be optionally substituted. As used herein, the term "substituted" is contemplated to include all permissible substituents of organic compounds, "permissible" being in the context of the chemical rules of valence known to those of ordinary skill in the art. It will be understood that "substituted" also includes that the substitution results in a stable compound, e.g., which does not spontaneously undergo transformation such as by rearrangement, cyclization, elimination, etc. In some cases, "substituted" may generally refer to replacement of a hydrogen with a substituent as described herein, e.g., a drug or a peptide. However, "substituted," as used herein, does not encompass replacement and/or alteration of a key functional group by which a molecule is identified, e.g., such that the "substituted" functional group becomes, through substitution, a different functional group. For example, a "substituted phenyl group" must still comprise the phenyl moiety and cannot be modified by substitution, in this definition, to become, e.g., a pyridine ring. In a broad aspect, the permissible substituents include acyclic and cyclic, branched and unbranched, carbocyclic and heterocyclic, aromatic and nonaromatic substituents of organic compounds. Illustrative substituents include, for example, those described herein. The permissible substituents can be one or more and the same or different for appropriate organic compounds. For purposes of this invention, the heteroatoms such as nitrogen may have hydrogen substituents and/or any permissible substituents of organic compounds described herein which satisfy the valencies of the heteroatoms.

Examples of substituents include, but are not limited to, halogen, azide, alkyl, aralkyl, alkenyl, alkynyl, cycloalkyl, hydroxyl, alkoxyl, amino, nitro, sulfhydryl, imino, amido, phosphonate, phosphinate, carbonyl, carboxyl, silyl, ether, alkylthio, sulfonyl, sulfonamido, ketone, aldehyde, ester, heterocyclyl, aromatic or heteroaruomatic moieties, —CF3, —CN, aryl, aryloxy, perhaloalkoxy, aralkoxy, heteroaryl, heteroaryloxy, heteroarylalkyl, heteroaralkoxy, azido, amino, halide, alkylthio, oxo, acylalkyl, carboxy esters, -carboxamido, acyloxy, aminoalkyl, alkylaminoaryl, alkylaryl, alkylaminoalkyl, alkoxyaryl, arylamino, aralkylamino, alkyl sulfonyl, -carboxamidoalkylaryl, -carboxamidoaryl, hydroxy alkyl, haloalkyl, alkylaminoalkylcarboxy-, aminocarboxamidoalkyl-, cyano, alkoxyalkyl, perhaloalkyl, arylalkyloxyalkyl, and the like. The peptides described herein are inclusive of at least two amino acids connected by amide bond.

While several embodiments of the present invention have been described and illustrated herein, those of ordinary skill in the art will readily envision a variety of other means and/or structures for performing the functions and/or obtaining the results and/or one or more of the advantages described herein, and each of such variations and/or modifications is deemed to be within the scope of the present invention. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present invention is/are used. Those skilled in the art will recognize, or be able to ascertain using no more than routine experimentation, many equivalents to the specific embodiments of the invention described herein. It is, therefore, to be understood that the foregoing embodiments are presented by way of example only and that, within the scope of the appended claims and equivalents thereto, the invention may be practiced otherwise than as specifically described and claimed. The present invention is directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the scope of the present invention.

The indefinite articles “a” and “an,” as used herein in the specification and in the claims, unless clearly indicated to the contrary, should be understood to mean “at least one.”

The phrase “and/or,” as used herein in the specification and in the claims, should be understood to mean “either or both” of the elements so conjoined, i.e., elements that are conjunctively present in some cases and disjunctively present in other cases. Other elements may optionally be present other than the elements specifically identified by the “and/or” clause, whether related or unrelated to those elements specifically identified unless clearly indicated to the contrary. Thus, as a non-limiting example, a reference to “A and/or B,” when used in conjunction with open-ended language such as “comprising” can refer, in one embodiment, to A without B (optionally including elements other than B); in another embodiment, to B without A (optionally including elements other than A); in yet another embodiment, to both A and B (optionally including other elements); etc.

As used herein in the specification and in the claims, “or” should be understood to have the same meaning as “and/or” as defined above. For example, when separating items in a list, “or” or “and/or” shall be interpreted as being inclusive, i.e., the inclusion of at least one, but also including more than one, of a number or list of elements, and, optionally, additional unlisted items. Only terms clearly indicated to the contrary, such as “only one of” or “exactly one of,” or, when used in the claims, “consisting of,” will refer to the inclusion of exactly one element of a number or list of elements. In general, the term “or” as used herein shall only be interpreted as indicating exclusive alternatives (i.e. “one or the other but not both”) when preceded by terms of exclusivity, such as “either,” “one of,” “only one of,” or “exactly one of” “Consisting essentially of,” when used in the claims, shall have its ordinary meaning as used in the field of patent law.

As used herein in the specification and in the claims, the phrase “at least one,” in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase “at least one” refers, whether related or unrelated to those elements specifically identified. Thus, as a non-limiting example, “at least one of A and B” (or, equivalently, “at least one of A or B,” or, equivalently “at least one of A and/or B”) can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

In the claims, as well as in the specification above, all transitional phrases such as “comprising,” “including,” “carrying,” “having,” “containing,” “involving,” “holding,” and the like are to be understood to be open-ended, i.e., to mean including but not limited to. Only the transitional phrases “consisting of” and “consisting essentially of” shall be closed or semi-closed transitional phrases, respectively, as set forth in the United States Patent Office Manual of Patent Examining Procedures, Section 2111.03.

What is claimed is:

1. A method of treating a hemorrhage site in a patient in need thereof, comprising depositing a fluid configured to form a foam or gel in situ in a body cavity at or near the hemorrhage site, wherein the fluid expands, thereby applying pressure to the walls of the body cavity to provide hemostasis.

2. The method of claim 1, wherein the hemorrhage site is a pelvic wound.

3. The method of claim 1, wherein the body cavity is an intra-abdominal cavity.

4. The method of claim 1, wherein the hemorrhage site is in the pelvic cavity.

5. The method of claim 1, wherein the hemorrhage is an abdominal hemorrhage.

6. The method of claim 5, wherein the abdominal hemorrhage is the result of blunt force.

7. The method of claim 5, wherein the abdominal hemorrhage is an incompressible hemorrhage.

8. The method of claim 1, wherein the hemorrhage is a pelvic hemorrhage.

9. The method of claim 8, wherein the pelvic hemorrhage is an incompressible hemorrhage.

10. The method of claim 1, wherein treating the hemorrhage comprises the steps of: mixing a first composition comprising a multifunctional isocyanate with a second composition comprising a polyol comprising up to 50 wt % polyethylene oxide, up to 10 pphp of an amine catalyst, and up to 20 pphp of water; and depositing the fluid within the body cavity of the patient to form a foam in situ such that the resulting foam applies a pressure to the walls of the body cavity.

11. A method of treating a pelvic hemorrhage comprising the steps of: mixing a first composition comprising a multifunctional isocyanate with a second composition comprising a polyol comprising up to 50 wt % polyethylene oxide, up to 10 pphp of an amine catalyst, and up to 20 pphp of water; and depositing the fluid within the pelvic cavity of the patient to form a foam in situ such that the resulting foam achieves close apposition to the wound site and applies a pressure to the pelvic hemorrhage, thereby limiting blood flow from the hemorrhage.

* * * * *